United States Patent [19]

Bogdahn et al.

[11] Patent Number: 5,770,366
[45] Date of Patent: Jun. 23, 1998

[54] MELANOMA-INHIBITING PROTEIN

[75] Inventors: Ulrich Bogdahn, Würzburg; Reinhard Burrner, Bach; Brigitte Kaluza, Bad Heilbrunn, all of Germany

[73] Assignee: Boehringer Mannheim GmbH, Mannheim, Germany

[21] Appl. No.: 578,649
[22] PCT Filed: Jul. 19, 1994
[86] PCT No.: PCT/EP94/02369
   § 371 Date: Jan. 19, 1996
   § 102(e) Date: Jan. 19, 1996
[87] PCT Pub. No.: WO95/03328
   PCT Pub. Date: Feb. 2, 1995

[30]    Foreign Application Priority Data

Jul. 20, 1993 [DE] Germany ........................... 43 24 247.2

[51] Int. Cl.⁶ ............................ C12Q 1/68; C12N 15/12; C12N 5/08; C12N 5/10; C12N 1/21; C12N 1/00; A61K 38/17; C07K 14/425; C07K 16/18
[52] U.S. Cl. .................... 435/6; 435/320.1; 435/252.3; 435/254.33; 435/325; 435/366; 435/69.1; 435/172.3; 536/23.5; 530/350; 530/387.9; 514/12
[58] Field of Search ..................... 435/6, 69.1, 172.3, 435/254.1, 252.33, 366, 320.01, 252.3, 325; 536/23.5; 530/350, 387.9; 514/12

[56]                References Cited

PUBLICATIONS

Apfel, R., et al., "Purification and analysis of growth regulating proteins, secreted by a human melanoma cell line", *j. Cell.. Biochem.*, Suppl. 16B:149 (1992).

Apfel, R., et al., "Tumor progression associated proteins are secreted by a human malignant melanoma cell line", *Proceedings of the American Association for Cancer Research* vol. 33:71 (1992).

Blesch, A., et al., "Cloning of a novel malignant melanoma–derived growth regulatory protein, MIA", *Cancer Res.* 54:5695–5701 (1994).

Blesch, A., et al., "Effects of Melanoma Inhibitory Activity upon growth of various tumour cell lines in vitro",*J. Cancer Res. Clin. Oncol.* 120:Supl. R112 (1994).

Blesch, A., et al., "Expression and Function of a novel, potent malignant melanoma cell growth inhibitor (MIA", *Proceedings of the American Association for Cancer Research* 35:567 (3379A) (1994).

Blesch, A., et al., "Cloning of a novel malignant melanoma cell growth inhibitor (MIA) and expression pattern in neuroectoderm derived tumor cell lines", *Journal of Neurooncology* 21:51 (1994).

Bogdahn, U., et al., "Autocrine tumor growth inhibiting activity from human malignant melanoma", *EMBL—Conference Oncogenes and Growth Control,* Heidleberg, EMBO Verlag, p. 23 (1988).

Behl, C., et al., "Biological characterization of a novel neuroectodermal–derived tumour growth inhibitor, melanoma–inhibiting activity", *Second Meeting of the European Neurological Society,* Brighton, england, UK, Jun. 30–Jul. 5, 1990, *J. Neurol.* 237 (Suppl. 1):S4 (1990).

Bogdahn, U., et al., "Melanoma inhibitory activity (MIA)—a new potent tumour growth regulatory protein",*J. Cancer Res. Clin. Oncol.* 120:Supl. R113 (1994).

Bosserhoff, A.-K., et al., "Inhibition of melanoma cell proliferation and invasion by human and murine MIA (melanona inhibiting activity)", *J. Invest. Dermatol.* 103(3):430 (1994).

Bosserhoff, A.-K., et al., "Inhibition of melanoma cell invasion by human and murine MIA (melanoma inhibitory activity)", *Proceedings of the AACR* 35:253 (1994).

Bosserhoff, A.-K., et al., "Molecular cloning and characterization of a new protein with melanoma inhibiting activity (MIA)", *Arch. of Dermatolog. Res.* 286(3/4):213–214 (1994).

U. Bogdahn et al., Autocrine Tumor Cell Growth–inhibiting Activities from Human Malignant Melanoma, Cancer Research 49, 5358–53–63, Oct. 1, 1989.

R. Apfel et al., "Purification and analysis of growth regulating proteins secrted by a human melanoma cell line", Melanoma Research, vol. 2, 1992, pp. 327–336.

F.X. Welbach, et al., Melanoma–inhibiting Activity Inhibits Cell Proliferation by Prolongation of the S Phase and Arrest of Cells in the G2 Compartment, Cancer Reserach 50, 6981–6986, Nov. 1, 1990.

*Primary Examiner*—Robert A. Wax
*Assistant Examiner*—G. E. Bugaisky
*Attorney, Agent, or Firm*—Felfe & Lynch

[57]                ABSTRACT

The invention concerns a melanoma-inhibiting protein, nucleic acid sequences coding for this protein, process for the isolation of this protein as well as its use for the production of a therapeutic agent.

27 Claims, 7 Drawing Sheets

MELANOMA-INHIBITING PROTEIN

FIELD OF THE INVENTION

The invention concerns a melanoma-inhibiting protein (MIA), a nucleic acid which codes for it, a process for the isolation and for the detection of this protein as well as its use for the production of a therapeutic agent.

BACKGROUND AND PRIOR ART

The regulation of cell growth is controlled by factors which act positively as well as negatively. The factors with a positive effect include the known growth factors such as e.g. epidermal growth factor (EGF), platelet derived growth factor (PDGF), insulin and somatomedins. The factors with a negative i.e. inhibitory activity include, in addition to TGF-β which can act as a growth stimulator as well as a growth inhibitor (Roberts et al., Proc. Natl. Acad. Sci. 82 (1985), 119–123), the endogenous, tumour-inhibiting factors from colon carcinoma cells (Levine et al., Cancer Research 45 (1985), 2248–2254), melanomas (Bogdahn et al., Cancer Research 49 (1989), 5358–5363) as well as from healthy epithelial cells from the mammary glands of the rat (Ethier et al., J. Cell. Phys. 142 (1990), 15–20).

Disturbances of this regulatory system such as for example by overproduction of growth factors with a positive action or by a reduced dependence of mutated cells on these growth factors (Rodeck et al., International Journal of Cancer 40 (1987), 687–690) enable tumour cells to proliferate in an uncontrolled manner. The aforementioned tumour-inhibitory factors from various tumour tissues represent interesting compounds which may be able to intervene therapeutically in this impaired regulatory system. It must be possible to provide these factors in large amounts and in reproducible purity for such a therapeutic use. However, for most of these factors only enriched fractions from cell lysates have been described up to now which are not suitable for a therapeutic application due to their complex and sometimes unknown composition and the concomitant non-reproducibility of their production.

SUMMARY OF THE INVENTION

The invention is based on a new melanoma-inhibiting protein (denoted MIA protein, or MIA, in the following) which inhibits growth of the cell lines HTZ 19-dM and ATCC CRL 1424 and
 a) is coded by the DNA sequence shown in SEQ ID NO: 1 for the mature protein or for the protein with a N-terminal pre sequence, or by the genomic sequence shown in SEQ ID NO: 3,
 b) is coded by DNA sequences which hybridize with the DNA sequences shown in SEQ ID NO: 1 or 3 or fragments of these DNA sequences in the DNA region which codes for the mature protein.

Growth inhibition is to be understood as an anti-proliferative activity. In this process the growth of the cells is considerably retarded by addition of the MIA protein to the culture medium. A suitable concentration for this is for example 0.1 μg MIA protein/ml culture medium. Higher or lower concentrations of the MIA protein are, however, also suitable for growth inhibition which is observed to be higher or lower depending on the concentration.

The properties of such a protein are described by the inventors in Cancer Research 49 (1989), 5358–5363, Cancer Research 50 (1990), 6981–6986, Melanoma Research 2 (1992), 327–336. However, a process for the production of this protein which can be reproduced is not stated in these publications. The protein is obtainable from the human melanoma cell line HTZ 19-dM which was previously not yet available to the public. This cell line was derived from a metastizing malignant melanoma and cultured as a monolayer culture in a defined serum-free culture medium (50% Dulbecco's minimal essential medium, 50% F-12) containing 0.8 mmol/l L-glutamine, non-essential amino acids, 10 μg/ml transferrin, 30 nmol/l sodium selenite and 4 μg/ml gentamicin under standard culture conditions. The cell line was deposited at the "Deutsche Sammlung für Mikroorganismen und Zellkulturen GmbH" in Braunschweig on the 23.06.93 (DSM ACC 2133). It is also a further subject matter of the invention. The protein according to the invention can be obtained from the culture supernatant of this cell line by gel chromatographic isolation of a protein fraction having a size of ca. 11 kD and subsequent purification of this fraction by means of reverse phase HPLC.

The protein can be defined by its DNA sequence and by the amino acid sequence derived therefrom. The MIA protein can occur in natural allelic variations which differ from individual to individual (e.g. SEQ ID NO: 24). Such variations of the amino acids are usually amino acid substitutions. However, they may also be deletions, insertions or additions of amino acids to the total sequence. The MIA protein according to the invention—depending, both in respect of the extent and type, on the cell and cell type in which it is expressed—can be in glycosylated or non-glycosylated form.

The protein according to the invention can also be produced by recombinant means. Non-glycosylated MIA protein is obtained when it is produced recombinantly in prokaryotes. With the aid of the nucleic acid sequences provided by the invention it is possible to search for the MIA gene or its variants in genomes of any desired cells (e.g. apart from human cells, also in cells of other mammals), to identify these and to isolate the desired gene coding for the MIA protein. Such processes and suitable hybridization conditions are known to a person skilled in the art and are described for example by J. Sambrook in Molecular cloning, Cold Spring Harbor Laboratory, 1989 and B. D. Hames, S. G. Higgins, Nucleic acid hybridisation—a practical approach (1985) IRL Press, Oxford, England. In this case the standard protocols described in these publications are usually used for the experiments.

The use of recombinant DNA technology enables the production of numerous MIA protein derivatives. Such derivatives can for example be modified in individual or several amino acids by substitution, deletion or addition. The derivatization can for example be carried out by means of site directed mutagenesis. Such variations can be easily carried out by a person skilled in the art (J. Sambrook, B. D. Hames, Loc. Lit.). It merely has to be ensured that the characteristic properties of the MIA protein (inhibition of the aforementioned cell lines) is preserved.

The invention therefore in addition concerns a MIA protein which
 a) is a product of a prokaryotic or eukaryotic expression of an exogenous DNA,
 b) is coded by the DNA sequence shown in SEQ ID NO: 1 for the mature protein or for the protein with an N-terminal pre sequence, the genomic sequence shown in SEQ ID NO: 3,
 c) is coded by DNA sequences which hybridize with the DNA sequences shown in SEQ ID NO: 1 or 3 or fragments of the DNA sequences in the DNA region which codes for the mature protein, or d) is coded by DNA sequences which if there was no degeneracy of the genetic code, would hybridize with the sequences defined in b) to c) and code for a polypeptide with amino acid sequence.

A protein is preferred which is coded by nucleotides 40–432 or 112 to 432 from SEQ ID NO: 1, or by DNA sequences which due to genetic code degeneracy would code for a polypeptide with the same amino acid sequence.

The MIA protein from HTZ 19-dM has a molecular weight of ca. 11 kD, is thermo-stable (3 minutes at 100° C.) and is sensitive towards proteases such as e.g. trypsin.

The invention concerns a nucleic acid which codes for a MIA protein and is selected from the group
a) DNA sequences shown in SEQ ID NO: 1 and 3 or the complementary sequences,
b) nucleic acid sequences which hybridize with one of the sequences from a),
c) nucleic acid sequences which, if there was no degeneracy of the genetic code, would hybridize with one of the sequences stated in a) or b).

The invention additionally concerns melanoma-inhibiting proteins from mammalian cells, such as, e.g., mouse, rat, bovine animal, sheep, which inhibit in an essentially analogous manner the growth of the cell lines HTZ19-dM and ATCC CRL1424, such as the human MIA protein.

These proteins which are analogous to the human MIA protein can be obtained by screening a cDNA library of the respective mammalian with a hybridization sample containing sequences coding for human MIA, according to methods familiar to the skilled artisan, carrying out a sequence comparison of the DNA and the protein sequence for human and murine MIA (SEQ ID NO: 1–5) and identifying the coding fragment.

A preferred embodiment of the invention is the murine MIA protein and the nucleic acid sequence coding therefor (SEQ ID NO:4). The murine protein is coded by nucleotides 110–499 or 179–499 of SEQ ID NO: 4.

With the aid of these nucleic acids the protein according to the invention can be obtained in a reproducible manner and in large amounts. For expression in prokaryotic or eukaryotic organisms, such as prokaryotic host cells or eukaryotic host cells, the nucleic acid is integrated into suitable expression vectors, according to methods familiar to a person skilled in the art. Such an expression vector preferably contains a regulatable/inducible promoter. These recombinant vectors are then introduced for the expression into suitable host cells such as e.g. *E. coli* as a prokaryotic host cell or Saccharomyces cerevisiae, Terato carcinoma cell line PA-1 sc 9117 (Büttner et al., Mol. Cell. Biol. 11 (1991) 3573–3583), insect cells, CHO or COS cells as eukaryotic host cells and the transformed or transduced host cells are cultured under conditions which allow an expression of the heterologous gene. The isolation of the protein can be carried out according to known methods from the host cell or from the culture supernatant of the host cell. Such methods are described for example by Ausubel I., Frederick M., Current Protocols in Mol. Biol. (1992), John Wiley and Sons, New York. Also in vitro reactivation of the protein may be necessary.

A DNA with the nucleotides 40–432 or 112–432 (coding sequence) of SEQ ID NO: 1 (cDNA) or the genomic DNA according to SEQ ID NO: 3 is preferably used for the recombinant production of the protein according to the invention.

In addition the invention concerns a process for obtaining a MIA protein by isolation of the culture supernatant of the melanoma cell line HTZ 19-dM by means of a gel chromatographic separation and purification of a fraction which corresponds to a molecular weight of ca. 11 kD (SDS-PAGE, non-reduced) by means of reverse phase HPLC. Ca. 0.2 µg/l culture supernatant can be obtained in this way.

In a preferred embodiment, the natural MIA protein, during isolation and purification, is subjected to acid treatment. By this, the MIA activity can be enhanced. Advantageously, a pH value of about 2 is applied; as acid, e.g., acetic acid is suitable.

The detection of transformed or transduced host cells which recombinantly produce the MIA protein and the purification of the protein are preferably carried out by means of antibodies which bind to this protein. Such antibodies can be obtained in a simple manner according to known methods by using the protein according to the invention as an antigen or an immunogen.

The invention therefore in addition concerns the use of the protein with melanoma-inhibiting activity according to the invention for the production of antibodies which bind to this protein.

For this animals which are usually used for this purpose, such as in particular, sheep, rabbits or mice, are immunized with the protein according to the invention and subsequently the antiserum is isolated from the immunized animals according to known methods or spleen cells of the immunized animals are fused with immortalized cells, such as e.g. myeloma cells, according to the method of Köhler and Milstein (Nature 256 (1975), 495–497). Those cells which produce a monoclonal antibody against the MIA protein are selected from the hybridoma cells obtained in this way and cloned. The monoclonal or polyclonal antibodies obtained in this way can be bound to a support material, such as e.g. cellulose, for an immunoabsorptive purification of the melanoma-inhibiting protein. Furthermore antibodies of this kind can be used for the detection of the MIA protein in samples, such as e.g. cut tissue or body fluids.

The invention therefore additionally concerns antibodies against the MIA protein which are obtainable by immunizing an animal with a MIA protein and isolating the antibodies from the serum or spleen cells of the immunized animals.

It has turned out that the MIA protein not only exhibits an inhibitory activity on melanoma cells but also, to a smaller extent, on other tumour cells such as e.g. glioblastoma cells, neuroblastomas, small cell lung cancer and neuroectodermal tumours by inhibiting DNA synthesis ($^3$H-thymidine incorporation (Coligan J. E., Kruisbeek A. M., Margulies D. H., Shevach E. M., Strober W., Current Protocols Immunology, NIH Monograph, J. Wiley and Sons, New York, 1992)), inhibiting tumour colony formation in soft agar or in a tumour stem cell assay (Schlag P., Flentje D., Cancer Treatment Rev. 11: Suppl. A: 131–137, 1984). In contrast the growth of normal non-degenerate cells is not inhibited. This protein acts already at very low concentrations (nanogram range). This protein is therefore suitable for the production of a therapeutic agent for tumour therapy. Such a therapeutic agent is particularly suitable for the therapy of malignant melanomas, malignant gliomas, bronchial carcinomas (in particular small cell bronchial carcinoma, SCLC) and neuroblastomas.

It has in addition turned out that the melanoma-inhibiting protein suppresses the interleukin 2-dependent and phytohaemagglutinin-induced proliferation of peripheral blood lymphocytes. The cytotoxicity of T lymphocytes is also reduced. The melanoma-inhibiting protein is thus also suitable for the production of a therapeutic agent which can be used as an immuno-suppressive agent.

The invention therefore in addition concerns the use of a protein according to the invention for the production of a therapeutic agent which can be used in tumour therapy or as an immunosuppressive agent.

The protein according to the invention is processed, if desired together with the usually used auxiliary agents, fillers and/or additives, in a pharmaceutical formulation for the said therapeutic applications.

The invention therefore in addition concerns a therapeutic composition containing a melanoma-inhibiting protein according to the invention and if desired together with the auxiliary agents, fillers and/or additives that are usually used.

The invention further concerns the use of sequences of the MIA gene, preferably sequences coding for a protein having MIA activity, or activating sequences from the 5' untranslated region, in gene therapy, and in particular, for the production of medicaments for gene therapy.

Gene therapy of somatic cells can be accomplished by using, e.g., retroviral vectors, other viral vectors, or by non-viral gene transfer (for clarity cf. T. Friedmann, Science 244 (1989) 1275; Morgan 1993, RAC DATA MANAGEMENT REPORT, June 1993).

Vector systems suitable for gene therapy are, for instance, retroviruses (Mulligan, R. C. (1991) in Nobel Symposium 8: Ethiology of human disease at the DNA level (Lindsten, J. and Pattersun Editors), pages 143–189, Raven Press), adeno associated virus (McLughlin, J. Virol. 62 (1988), 1963), vaccinia virus (Moss et al., Ann. Rev. Immunol. 5 (1987) 305), bovine papilloma virus (Rasmussen et al., Methods Enzymol. 139 (1987) 642) or viruses from the group of the herpes viruses such as Epstein Barr virus (Margolskee et al., Mol. Cell. Biol. 8 (1988) 2937) or Herpes simplex virus.

There are also known non-viral delivery systems. For this, usually "nude" nucleic acid, preferably DNA, is used, or nucleic acid together with an auxiliary such as, e.g., transfer reagents (liposomes, dendromers, polylysine-transferrine-conjugates (Wagner, 1990; Felgner et al., Proc. Natl. Acad. Sci. USA 84 (1987) 7413)).

Another preferred method of gene therapy is based on homologous recombination. In this, either the gene coding for the MIA protein can be inserted in one or more copies into the genome of somatic cells and/or the MIA gene endogenously present in the cells can be modulated, preferably activated.

Methods of homologous recombination are described, e.g., in Kucherlapati, Proc. in Nucl. Acids Res. and Mol. Biol. 36 (1989) 301; Thomas et al., Cell 44 (1986) 419–428; Thomas and Capecchi, Cell 51 (1987) 503–512; Doetschman et al., Proc. Natl. Acad. Sci. USA 85 (1988) 8583–8587 and Doetschman et al., Nature 330 (1987) 576–578. In these methods, a portion of DNA to be ingrated at a specific site in the genome (gene fragment of MIA) is bound to a targeting DNA. The targeting DNA is a DNA which is complementary (homologous) to a region (preferably within or proximal to the MIA gene) of the genomic DNA. When two homologous portions of a single-stranded DNA (e.g. the targeting DNA and the genomic DNA) are in close proximity to one another they will hybridize and form a double-stranded helix. Then the MIA gene fragment and the targeting DNA can be integrated into the genome by means of occurrence of recombination. This homologous recombination can be carried out both in vitro and in vivo (in the patient).

Preferably, there is used a DNA which codes for a protein having MIA activity, a fragment which inhibits MIA expression (knock-out sequence) or a fragment capable of activating, after integration of the genome of a cell, expression, in this cell, of a protein having MIA activity.

Such a fragment may be, for example, a promoter and/or enhancer region which is heterologous to the corresponding MIA region or which, after integration into the MIA gene, activates the actually silent or to a little extent expressed MIA gene transcriptionally and/or translationally.

Thus, by means of this DNA, one or more MIA genes are newly introduced into the target cell, or the essentially transcriptionally silent gene in the genome of a mammalian cell is activated in such fashion that the mammalian cell is enabled to produce endogenous MIA protein. To this end, a DNA construct is inserted into the genome by homologous recombination, the DNA construct comprising the following: a DNA regulatory element capable of modulating, preferably stimulating, expression of this gene if operatively linked thereto; and one or more DNA target segments which are homologous to a region in this genome, which region is within or proximal to this gene. This construct is inserted into the genome of the mammalian cell in such fashion that the regulatory segment is operatively linked to the gene which codes for the protein having MIA activity. Preferably, the construct further comprises amplifying sequences, especially if genes coding for proteins with MIA activity are inserted into the cell.

For the introduction of MIA genes into the target cells, the construct comprises a regulatory element, one or more MIA genes and one or more target segments. The target segments are chosen in such a way that they hybridize with an appropriate region of the genome, whereby, after homologous recombination, the inserted exogenous MIA genes are expressed.

There are known a large number of processes by which homologous recombination can be initiated. Preferably, homologous recombination takes place during DNA replication or mitosis of the cells. A DNA of this kind can be used for the production of an agent for therapeutic treatment of tumours or for the production of homologous or heterologous MIA protein in a host organism.

It is possible to provide a test on the basis of the nucleic acid sequences of the MIA protein provided by the invention which can be used to detect nucleic acids which code for MIA proteins. Such a test can for example be carried out in cells or cell lysates. Such a test can be carried out by means of nucleic acid diagnostics. In this case the sample to be examined is brought into contact with a probe which would hybridize with the nucleic acid sequence coding for the MIA protein. A hybridization between the probe and nucleic acids from the sample indicates the presence of expressed MIA proteins. Such methods are known to a person skilled in the art and are for example described in WO 89/06698, EP-A 0 200 362, USP 2915082, EP-A 0 063 879, EP-A 0 173 251, EP-A 0 128 018.

In a preferred embodiment of the invention, the nucleic acid of the sample which codes for a MIA protein is amplified before testing, e.g. by the well-known PCR technique. A derivatized (labelled) nucleic acid probe is usually used in the field of nucleic acid diagnostics. This probe is brought into contact with a carrier-bound denatured DNA or RNA from the sample and in this process the temperature, ionic strength, pH value and other buffer conditions are selected in such a way that—depending on the length of the nucleic acid sample and the resulting melting temperature of the expected hybrid—the labelled DNA or RNA can bind to homologous DNA or RNA (hybridization, see also J. Mol. Biol. 98 (1975), 503; Proc. Natl. Acad. Sci. USA 76 (1979), 3683). Suitable carriers are membranes or carrier materials based on nitrocellulose (e.g. Schleicher and Schüll, BA 85, Amersham Hybond, C.) reinforced or bound nitrocellulose in a powder form or nylon membranes derivatized with various functional groups (e.g. nitro group) (e.g. Schleicher and Schüll, Nytran; NEN, Gene Screen; Amersham Hybond M.; Pall Biodyne).

The hybridized DNA or RNA is then detected by incubating the carrier, after thorough washing and saturation to prevent unspecific binding, with an antibody or antibody fragment. The antibody or antibody fragment is directed towards the substance incorporated into the nucleic acid probe during the derivatization. The antibody is in turn labelled. It is, however, also possible to use a directly labelled DNA. After incubation with the antibodies, it is washed again in order to only detect specifically bound antibody conjugates. The determination is then carried out via the label of the antibody or antibody fragment according to well-known methods.

The detection of the MIA expression can be carried out for example as:

in situ hybridization with immobilized whole cells using immobilized tissue smears and isolated metaphase chromosomes, colony hybridization (cells) and plaque hybridization (phages and viruses), Northern hybridization (RNA detection), serum analysis (e.g. cell type analysis of cells in serum by slot-blot analysis), after amplification (e.g. PCR technique).

The invention therefore includes a method for the detection of nucleic acids which code for a MIA protein which is characterized in that the sample to be examined is incubated with a nucleic acid probe which is selected from the group
a) the DNA sequences shown in SEQ ID NO 1 and 3 or a complementary sequence to these
b) nucleic acids which hybridize with one of the sequences from a),
the nucleic acid probe is incubated with the nucleic acid from the sample and the hybridization of the nucleic acid in the sample and nucleic acid probe is detected, if desired, via a further binding partner.

Thus, MIA is a valuable prognostic marker in tumour diagnostics (metastasis, progress).

The invention is elucidated in more detail by the sequence protocols in conjunction with the following examples and figures. In this case
SEQ ID NO: 1—denotes cDNA of human MIA with pre sequence
SEQ ID NO: 2—denotes protein
SEQ ID NO: 3—denotes genomic DNA of MIA.
SEQ ID NO: 4—denotes cDNA of murine MIA with pre sequence
SEQ ID NO: 5—denotes protein
SEQ ID NO: 6—denotes primer
SEQ ID NO: 7—denotes primer
SEQ ID NO: 8—denotes cloning fragment
SEQ ID NO: 9—denotes primer
SEQ ID NO: 10—denotes primer
SEQ ID NO: 11—denotes adaptor
SEQ ID NO: 12—denotes adaptor
SEQ ID NO: 13—denotes fusion protein
SEQ ID NO: 14—denotes fusion protein
SEQ ID NO: 15—denotes primer
SEQ ID NO: 16—denotes primer
SEQ ID NO: 17—denotes primer
SEQ ID NO: 18—denotes fusion-free MIA for expression in E. coli
SEQ ID NO: 19—denotes primer
SEQ ID NO: 20—denotes primer
SEQ ID NO: 21—denotes primer
SEQ ID NO: 22—denotes primer
SEQ ID NO: 23—denotes polylinker
SEQ ID NO: 24—denotes genomic DNA of MIA (allelic variant)

BRIEF DESCRIPTION OF THE FIGURES

| FIG. 1 | depicts the invasion-inhibitory activity of human MIA (inhibition of movement of the cells with and without MIA, in %). B 16 + mMIA: Test using murine MIA |
| --- | --- |
| FIG. 2A and 2B | depict the inhibition of T-cell mediated cytotoxic activity by MIA, expressed as % lysis of CD4$^+$ T cells. |
| FIG. 3 | depicts the inhibition of the cytotoxic acitivity of LAK-cells by MIA. |
| FIG. 4 | depicts the inhibition of the phytohaemagglutinin-dependent lymphocyte proliferation by MIA (concentration of MIA expressed as ng/ml). |
| FIG. 5 | depicts the inhibition of the IL-2 stimulated PBMC proliferation by MIA (concentration of MIA expressed as ng/ml). |
| FIG. 6 | shows a plasmid chart of the expression plasmid pQE40-MIA (Example 5a). |
| FIG. 7 | shows a plasmid chart of the vector pCMX-PL1 (Example 7a). |

DETAILED DESCRIPTION OF PREFERRED EMBODIMENTS

EXAMPLE 1

Figure 1:
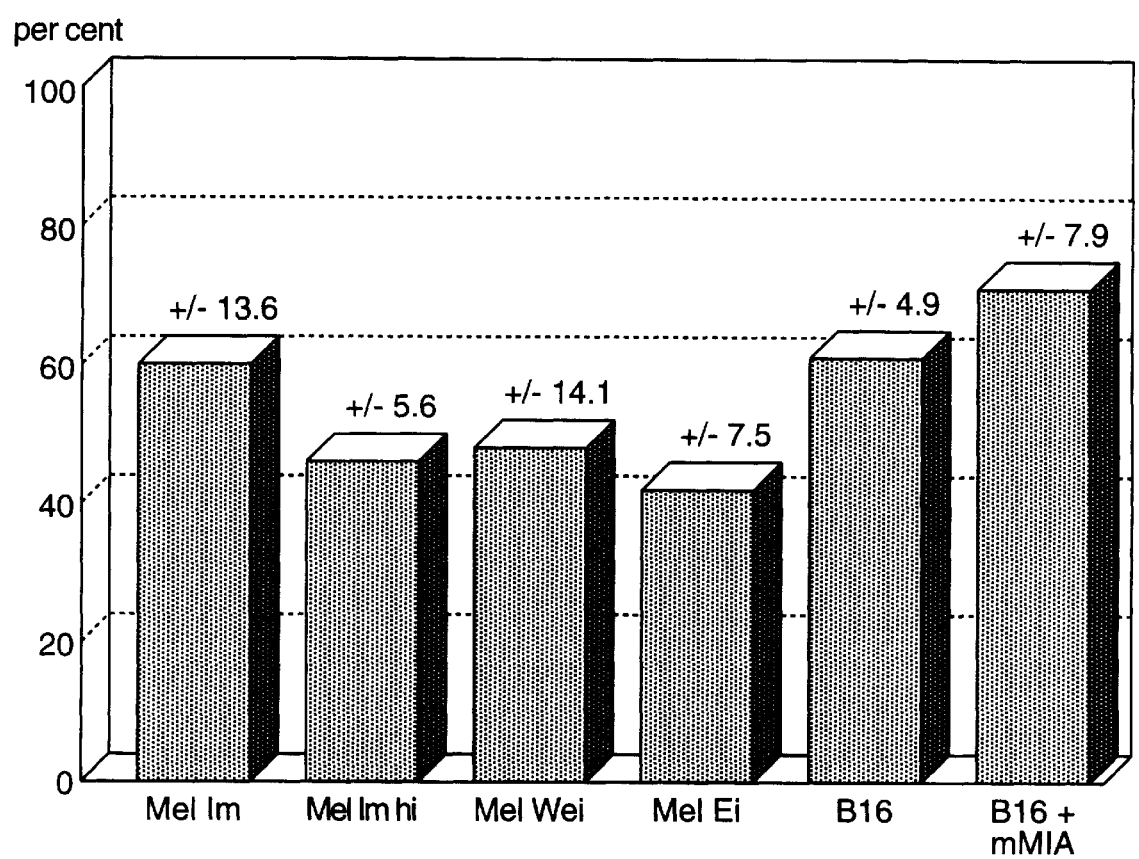

Isolation of the melanoma-inhibiting protein from HTZ 19-dM cells.

HTZ 19-dM cells are cultured as a monolayer in defined serum-free tissue culture medium (50% Dulbecco's minimal essential medium, 50% F-12, Boehringer Mannheim GmbH) containing 0.8 mmol/l L-glutamine (Gibco, U.K.), non-essential amino acids (Gibco, U.K.), 10 µg/ml transferrin (Boehringer Mannheim GmbH, Catalogue No. 1073974), 30 nmol/l sodium selenite (Sigma) and 4 µg/ml Gentamicin (Merck). The cell culture supernatant of this culture is removed at intervals of 3 to 4 days in each case and stored at −70° C. until purification.

For purification, the cell culture supernatants are filtered through a 0.45 µm filter (Becton Dickinson, Heidelberg) and concentrated by membrane ultrafiltration using Amicon YM 2 membranes (exclusion limit 2000 D, Amico Danvers Mass., USA) to a final volume of 1% of the initial volume. The material obtained is dialysed for 30 hours against 0.1 mol/l acetic acid (dialysis membrane with an exclusion limit of 1000 D, Reichelt, Heidelberg) and subsequently ultracentrifuged at 100,000 g for one hour at 4° C. The pellet is discarded and the supernatant is lyophilized for further processing.

The lyophilized dialysates are taken up in 1 mol/l acetic acid and purified further by gel permeation chromatography on a Biogel P-10 column (Pharmacia, Uppsala, 2.6×100 cm; Biogel P-10, 200–400 mesh, Biorad Laboratories, Richmond, Calif., USA). The gel material is equilibrated with 1 mol/l acetic acid at 22° C. and the dialysates are applied at a concentration of 130–145 mg in 5 ml 1 mol/l acetic acid. It is eluted with 1 mol/l acetic acid at a flow rate of 12 ml/hour and the eluate is collected in 4 ml fractions. Three active fraction pools are defined by determination of the anti-tumour activity (cf. example 5) of which the middle pool which corresponds to a molecular weight of 8000–17000 D is purified further by means of reverse HPLC. For this these fractions are firstly lyophilized once and then taken up in 0.1% trifluoro-acetic acid (TFA). 100 µl aliquots of the solution obtained are applied in each case to the reverse phase HPLC (flow rate 0.5 ml/min). Fractions of 750 µl in each case are collected. Further data concerning the HPLC separation:

Gradient program:
 solution A: 0.06 TFA in water
 solution B: 0.056% TFA, 80% acetonitrile
2–25% solution B within 5 min
25–50% solution B within 120 min
50–100% solution B within 5 min return to 2% within 5 min
column: minoRPC (Pharmacia)
HPLC gradient mixer, pump and detector: Pharmacia The eluate is collected in 1.5 ml fractions. Aliquots are lyophilized and examined for anti-tumour activity as described in example 5.

Ca. 1 µg melanoma-inhibiting protein can be obtained in this manner from 5 l culture supernatant.

EXAMPLE 2

EXAMPLE 2a

Cloning the cDNA coding for the human melanoma-inhibiting protein

The MIA amino acid sequences are determined in a sequencer after Asp-N and trypsin digestion of the purified protein and repurification of the peptide fragments obtained in this manner. The C-terminal peptide sequence and one located near to the N-terminus were selected as the basis for the synthesis of two primers. The primers are degenerate oligonucleotides with added restriction enzyme cleavage sites.

Upstream primer 1 (sense) (UP 1)    (SEQ ID NO: 6)

5'TGTGAATTCAGTTIA/TG/CIGCIGAT/CCAA/GGAA/GTG 3' EcoRI site

The diagonal stroke (/) denotes that the base at this position is located either in front of or behind the diagonal stroke. This oligonucleotide is a mixture of 32 different molecules thereby covering almost all possible codons. G-T mismatches with the target sequence can only occur at positions 12 and 13 which does not increase the stability of the hybrids but does not reduce it either. An EcoRI linker is additionally attached to the 5' end in order to be able to easily reclone a possible product by PCR. A further 3 unspecific bases are located in front of this at the 5' end in order that the restriction cleavage site is not quite at the end since restriction enzymes do not cleave very well at this position.

Downstream primer 1 (antisense) (DP1)    (SEQ ID NO: 7)

5'TGTGTCGACTGTTCGTAGAAA/GTCCCATCTTA/GTC 3' SalI site

DP 1 corresponds to 8 the C-terminal amino acids, is 8-fold degenerate and contains a Sal I cleavage site.

The primer DP 1 was used in the following mixture for the specific first strand synthesis:

5 µl 10×PCR buffer
3 µl HTZ-19 total RNA was mixed and heated for 5 min to 65° C.

The following were added by pipette:

1 µl 100 mM MgCl$_2$
10 µl 2.5 mM dNTP
0.5 µl placental RNase inhibitor
2 µl DP 1 (1 µg)
1 µl reverse transcriptase.

After 1 h incubation at 37° C. the following were added to the above mixture:

1 µl UP 1 (1 µg)
5 µl 10×PCR buffer
70.5 µl H$_2$O
1 µl Taq polymerase

The amplification was carried out in 30 cycles with the following profile:

94° C. 30 sec.
 55° C. 30 sec.
 72° C. 60 sec.

After the last cycle the mixture was incubated for a further 7 minutes at 72° C. for the complete elongation of all products.

After a phenol/chloroform extraction and EtOH precipitation, the PCR mixture was digested with EcoRI and SalI for 2 hours at 37° C. After enzyme activation, it was subsequently separated in a 5% PAA gel and the 320 bp fragment was eluted overnight. Half the eluate was ligated overnight with 100 ng EcoRI/SalI digested pbluescript. It was possible to pick a recombinant white colony from the bacteria (E. coli DH5a) which were transformed on the next day and plated out on SOB agar plates containing Amp and X-Gal/IPTG.

After isolation of the plasmid, sequencing of the recloned insert was carried out using the T-7 Deaza sequencing kit from Pharmacia. The T-3 and T-7 primers (Stratagene) were available as primers. The following picture emerged from the overlap of the read sequences (primers are in print):

(SEQ ID NO:8)

```
GAATTC AAG TTT TCG GCG GAT CAG GAG TGC AGC CAC CCT ATC TCC ATG
EcoR1  Lys Phe Ser Ala Asp Gln Glu Cys Ser His Pro Ile Ser Met

GCT GTG GCC CTT CAG GAC TAC ATG GCC CCC GAC TGC CGA TTC CTG ACC
Ala Val Ala Leu Gln Asp Tyr Met Ala Pro Asp Cys Arg Phe Leu Thr

ATT CAC CGG GGC CAA GTG GTG TAT GTC TTC TCC AAG CTG AAG GGC CGT
Ile His Arg Gly Gln Val Val Tyr Val Phe Ser Lys Leu Lys Gly Arg

GGG CGG CTC TTC TGG GGA GGC AGC GTT CAG GGA GAT TAC TAT GGA GAT
Gly Arg Leu Phe Trp Gly Gly Ser Val Gln Gly Asp Tyr Tyr Gly Asp

CTG GTC GCT CGC CTG GGC TAT TTC CCC AGT AGC ATT GTC CGA GAG GAC
Leu Val Ala Arg Leu Gly Tyr Phe Pro Ser Ser Ile Val Arg Glu Asp
```

-continued

| CAG | ACC | CTG | AAA | CCT | GGC | AAA | GTC | GAT | GTG | AAG | ACA | GAT | AAA | TGG | GAT |
|---|---|---|---|---|---|---|---|---|---|---|---|---|---|---|---|
| Gln | Thr | Leu | Lys | Pro | Gly | Lys | Val | Asp | Val | Lys | Thr | Asp | Lys | Trp | Asp |

| TTC | TAC | GAA | CAGTCGAC |
|---|---|---|---|
| Phe | Tyr | Glu | SalI |

A lambda gt11 cDNA library was available for cloning the complete cDNA which had been synthesized from the RNA of HTZ-19 melanoma cells growing in a defined medium (dM).

A total of 25 plates each with 8000 pfu were plated out, 2 nitrocellulose filters were placed on each and they were hybridized with the purified MIA-PCR insert labelled by nick translation (50 ml hybridization solution, $2 \times 10^6$ cpm/ml). After a two-day autoradio-graphy, several signals were obtained which gave a corresponding hybridization signal on both filters. The corresponding phage-plaques were picked out and subjected to a rescreen. Four dilution steps of each isolated plaque were plated out for this and the plates with 100–300 pfu were used for two further rescreens.

After a 50 ml overnight culture, the lambda DNA could be isolated from the plaques isolated in this manner, 40 μg thereof was digested with EcoRI and separated in a 5% PAA gel. The insert was eluted and 8 ng was used for ligation with 100 ng EcorRI-digested dephosphorylated vector (pbluescript, Stratagene). Half the ligation mixtures were used for the transformation of competent *E. coli* DH5a which were plated on SOB/Amp plates containing IPTG and X-Gal for the blue/white selection. The recombinant colonies were picked out, the plasmid DNA was isolated and the inserts were sequenced. The sequence of the insert with the complete coding sequence is shown in SEQ ID NO:1.

A plasmid obtained in this manner is pbs L7MIA which was deposited at the "Deutsche Sammlung für Mikroorganismen und Zellkulturen GmbH" (DSM) in Braunschweig, Germany on the 14.07.93 (DSM 8420).

All methods used for cloning are described in detail in J. Sambrook, E. F. Fritsch, T. Maniatis (1989), Molecular cloning: a laboratory manual, 2nd edition, Cold Spring Harbor Laboratory Press, Cold Spring Harbor, USA.

EXAMPLE 2b

Cloning the gene coding for the human melanoma-inhibiting protein

A human genomic DNA library in the bacteriophage lambda FIX II (Elgin et al., Strategies 4 (1991) 8–9) which is commercially available from Stratagene (Heidelberg), was plated on nitrocellulose filters according to the established methods (Sambrook et al., Molecular Cloning (1989), Cold Spring Harbor Laboratory Press). In order to be used as a hybridization sample, the cDNA from Example 2a coding for human MIA was radiolabelled and applied according to the established techniques (Sambrook et al., Molecular Cloning (1989), Cold Spring Habor Laboratory Press). Prehybridization (2 hours) and hybridization (16 hours) was carried out at 60° C. in 6×SSC, 5×Denhardt's solution, 100 μg/ml salmon sperm DNA and 0.1% SDS. The $^{32}$P-dCTP-labelled sample was added to the hybridization preparation at a concentration of $1 \times 10^6$ cpm/ml. Thereafter, the filters were washed at 60° C. two times for 20 minutes in 2×SSC, 0.1% SDS, then two times for 20 minutes in 1×SSC, 0.1% SDS, and finally, two times for 20 minutes in 0.25×SSC, 0.1% SDS. The filters were subsequently dried and then exposed to X-ray film for 24 to 48 hours. The plaques which, in this method, yielded a positive hybridization signal were isolated and confirmed by rehybridization.

The human genomic DNA contained as an insert in these phages was characterized by Southern hybridization using MIA cDNA samples. For this purpose the phage DNA was cleaved with the restriction endonuclease XbaI, separated on a 0.8% agarose gel, and subsequently transferred to nitrocellulose according to Southern (J. Mol. Biol. 98 (1975) 503). The so obtained filters were hybridized with the complete MIA cDNA as a sample under the above-described conditions, whereby two XbaI fragments of a size of about 1.4 kb and about 2.2 kb gave positive signals. Each of these two fragments was cloned into the plasmid pbluescriptSK- (Short et al., Nucl. Acids Res. 16 (1988) 7583–7600; Alting-Meese and Short, Nucl. Acids Res. 17 (1989) 9494) being suitable for sequencing and commercially available from Stratagene (Heidelberg). The entire sequence coding for human MIA is located in four exons which are shown with their flanking sequences in SEQ ID NO:3. Since it was not investigated whether there are one or even more additional XbaI fragments between the two XbaI fragments on which the MIA exons are located, it cannot be ruled out that intron 2 is in actual fact much larger.

EXAMPLE 2c

Cloning of the cDNA coding for the murine melanoma-inhibiting protein

A commercially available (Novagene, N.Y.) cDNA library from a 13.5 day-old mouse embryo in the vector lambda EXlox (Palazzolo et al., Gene 88 (1990) 25–36) was plated as described in Example 2a. As the hybridization sample there was employed, in radiolabelled form, the cDNA from Example 2a which codes for human MIA. The hybridization conditions were identical to those described in Example 2b, except for the temperatures applied during hybridization and wash, which were 55° C. here. The cDNA inserts present in the plaques so obtained and confirmed by rehybridization were sequenced. The sequence of the insert containing the complete coding DNA of the murine MIA is shown in SEQ ID NO:4.

EXAMPLE 2d

Cloning of the gene coding for the murine melanoma-inhibiting protein

In this case a murine genomic DNA library (from the liver of an adult BALB/C mouse in the vector EMBL3 (Frischauf et al., J. Mol. Biol. 170 (1983) 827), commercially available from Clontech, Palo Alto Calif.) was searched in a fashion analogous to Example 2b using the murine MIA cDNA from Example 2c as a sample. The conditions were identical to those described in Example 2b. Also the further proceeding was in analogous fashion.

EXAMPLE 3

EXAMPLE 3a

Determination of the antiproliferative effect of the melanoma-inhibiting protein on tumour cells In order to determine the antiproliferative effect of the melanoma-inhibiting protein or of the protein fractions obtained according to example 1 on melanoma cells, exponentially growing HTZ 19-dM cells are sown out for 24 hours in 96-well microculture plates (Costar, Zürich) each in 100 μl serum-free medium (see example 1) at a density of 3×10³ cells per well (according to Chambard et al., J. Cell. Physiol. 135 (1988), 101–107). The cells are then incubated with the protein fraction to be examined for 4–5 days at 37° C./5% $CO_2$. After addition of 1 μCi ³H-thymidine (specific activity 23 Ci/mmol, Amersham Buchler, Braunschweig, Germany) to each, the cells are incubated for a further 8 hours under identical conditions and subsequently the ³H-thymidine incorporation into the cellular DNA is measured after acid precipitation in the usual manner by means of a liquid scintillation counter. The activity of the examined protein fraction is expressed as a percentage of the ³H-thymidine incorporation of these treated cells compared to the ³H-thymidine incorporation in untreated control cells. By use of different concentrations of the isolated melanoma-inhibiting protein it is possible to determine a concentration at which this ³H-thymidine incorporation is inhibited by 50% compared to the untreated control, (IC 50 value in the following Table 1).

TABLE 1

Antiproliferative effect of the melanoma-inhibiting protein on various tumour cells

| Tumour cell line | IC 50 (μg/ml)[1] |
|---|---|
| a) melanoma cell lines | |
| HTZ 19-dM | 1.2 |
| ATCC HTB 69 | 3.7 |
| HTZ 320 | 1.35 |
| HTZ 318 | 3.5 |
| ATCC CRL 1424 | 2.1 |
| b) neuroblastoma lines | |
| Kelly | 80 |
| c) glioblastoma | |
| ATCC HTB17 | 10 |
| d) astrocytoma | |
| HTZ 243 | 5 |
| HTZ 209 | 5 |

[1]The protein obtained after the first purification step was used (after Biogel P10 column, 50–100-fold lower activity than after complete purification).

EXAMPLE 3b

Determination of the invasion-inhibiting effect of the melanoma-inhibiting protein on tumour cells In order to determine the invasion-inhibiting effect of MIA a modified Boyden Chamber System (Albini et al., Cancer Res. 47 (1987) 3239–3245) is used. The chambers were obtained from the firm Costar (Blind Well Chamber No. 441200). For simulation of a basement membrane-like barrier between the chemoattractant in the lower chamber and the cells in the upper chamber, 52 μl matrigel (Becton Dickinson Cat. No. 40234) are applied onto the polycarbonate filter (pore size 8 μm, Costar No. 150446). The lower chamber is filled with 210 μl fibroblast conditioned-medium as the chemoattractant. This medium is obtained according to the following procedure: fibroblasts from normal human skin are maintained between the 10th and the 20th passage in DMEM medium (Gibco) for 24 hours without addition of fetal calf serum. The so conditioned medium is applied in undiluted form as a chemoattractant. Into the upper chamber of the Boyden apparatus are applied 2×10⁵ of the tumour cells to be examined, in 800 μl DMEM (Gibco, without fetal calf serum), with and without MIA active ingredient. Human (see Example 3a or Example 8) or animal tumour cells such as, for example, B16 (ATCC CRL 6322) can be tested by the described method with respect to the inhibition of their migration behaviour through MIA. When no melanoma-inhibiting protein is added, about 10% of the tumour cells migrate within a period of about 4 hours from the upper chamber into the lower chamber where they stick to the lower side of the Matrigel membrane. There, they are fixed, dyed and subsequently counted. If the human or murine melanoma-inhibiting protein MIA is added to the upper chamber, then cell migration is strongly inhibited. FIG. 1 shows the inhibition values obtained ([cell count in lower chamber, experiment with MIA]-\ [cell count in lower chamber, experiment without MIA]×100%).

EXAMPLE 4

Determination of the immunological activity

EXAMPLE 4a

MIA inhibits T cell-mediated cytotoxic activity

Figure 2:
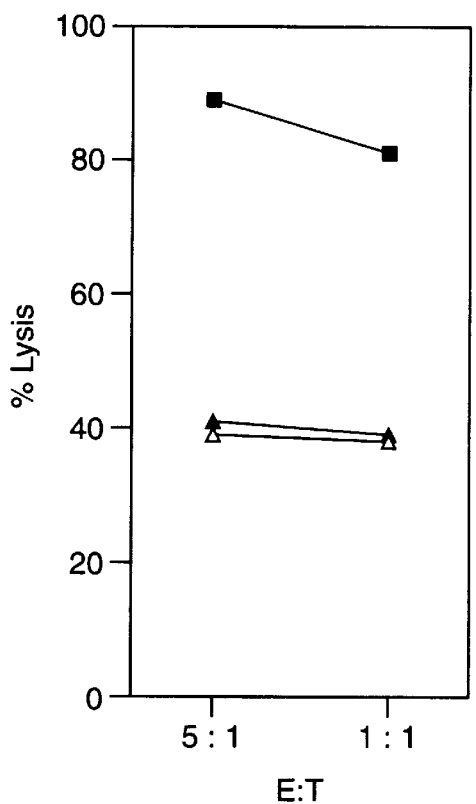
Figure 2:
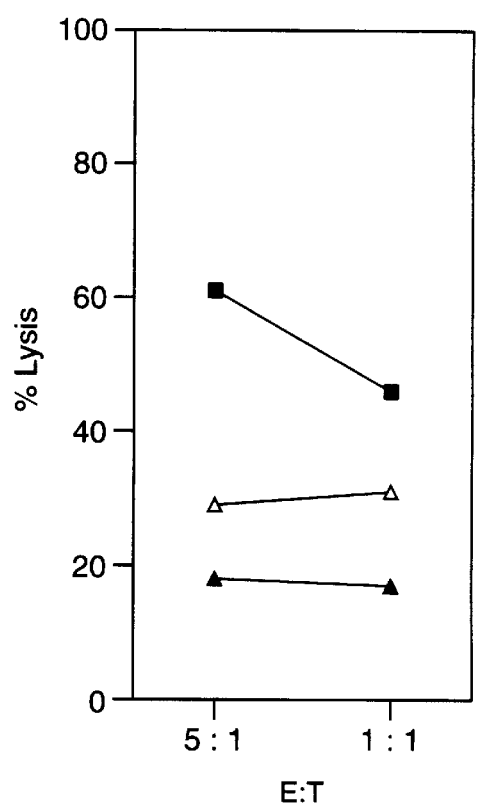

The $CD4^+$ T cell line D7.1 specific for MBP peptide 87–106 is able to lyse targets presenting MBP as well as peptide 87–106 in a standard $^{51}Cr$ release assay (targets: Daudi cells, R. Martin, U. Utz, J. E. Coligan, J. R. Richert, M. Flerlage, E. Robinson, R. Stone, W. E. Biddison, D. E. MacFarlin, H. F. MacFarland, Diversity in fine specificity and T cell receptor usage of the human $CD^{4+}$ cytotoxic T cell response specific for the immunodominant myelin basic protein peptide 87–106, J. Immunol. (1992), 148 (5), 1359–1366). After addition of MIA (amount used corresponds to ca. 50–100 ng/ml purified MIA), the peptide-specific cytotoxicity is inhibited by ca. 55% (FIG. 2a) and the MBP-specific cytotoxicity by ca. 50% (FIG. 2b). As expected the inhibition is slightly dependent on the effector-target ratio (E:T) which was set in this case at a very low level of 1:1 or 5:1 and is thus highly specific (FIG. 2).

EXAMPLE 4b

MIA inhibits the cytotoxic activity of lymphokine-activated peripheral blood lymphocytes (LAK cells)

Figure 3:
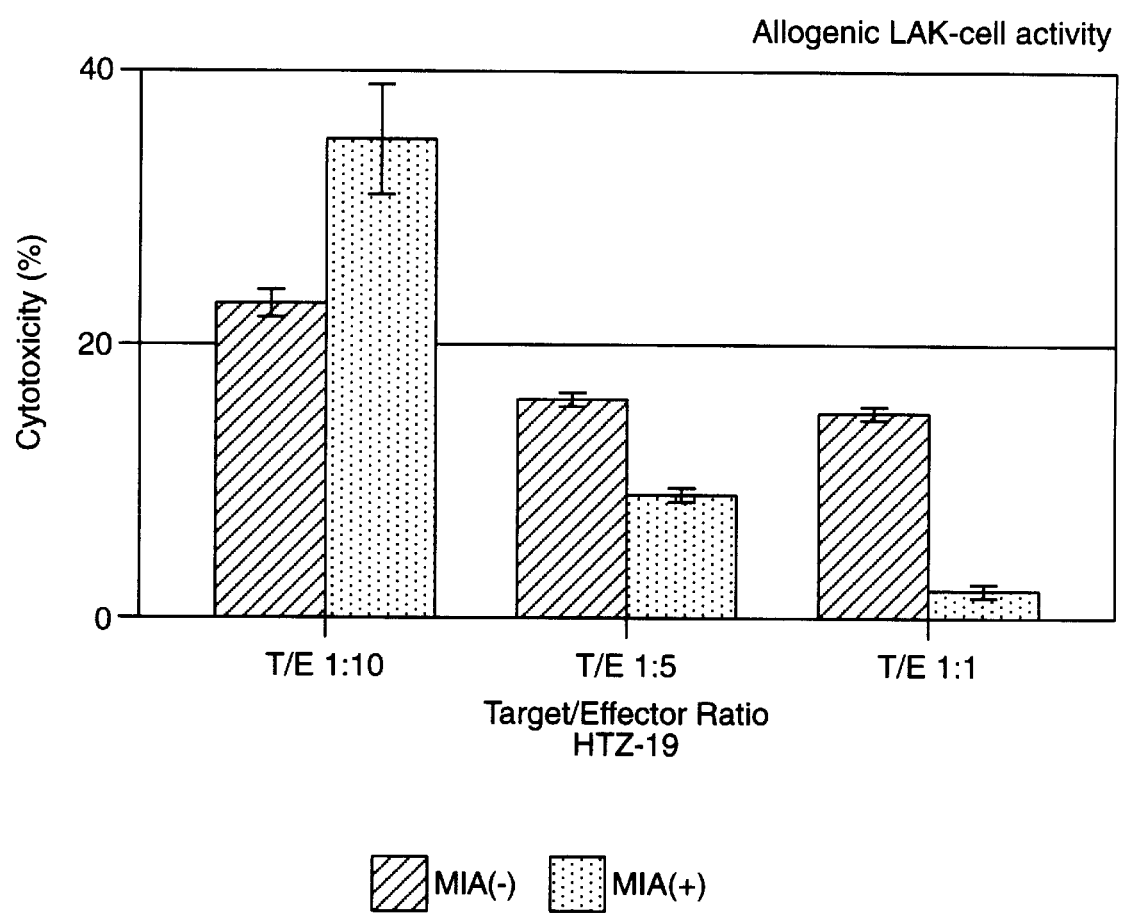

LAK cells are non-clonally expanded, lymphokine-activated peripheral blood lymphocytes, predominantly T lymphocytes (A. A. Rayner, E. A. Grimm, M. T. Lotze, E. W. Chu, S. A. Rosenberg, Lymphokine activated killer (LAK) cells: Analysis of factors relevant for immunotherapy of human cancer, Cancer 55 (1985), 1327–1333). They are used in a standard manner in many immunological therapy approaches for tumour therapy. In the experiment shown in this case, LAK cells are examined for their cytotoxicity towards HTZ-19 melanoma cells as targets in a microcytotoxicity assay. At effector-target ratios of 1:1, 5:1 and 10:1 the maximum cytotoxicity (CTX) reaches almost 40%. This is strongly inhibited after addition of MIA (concentration as in example 4a) and by a maximum of 80% at a low effector-target ratio which is more likely to be expected locally i.e.—near the tumour itself—(FIG. 3).

EXAMPLE 4c

Figure 4:
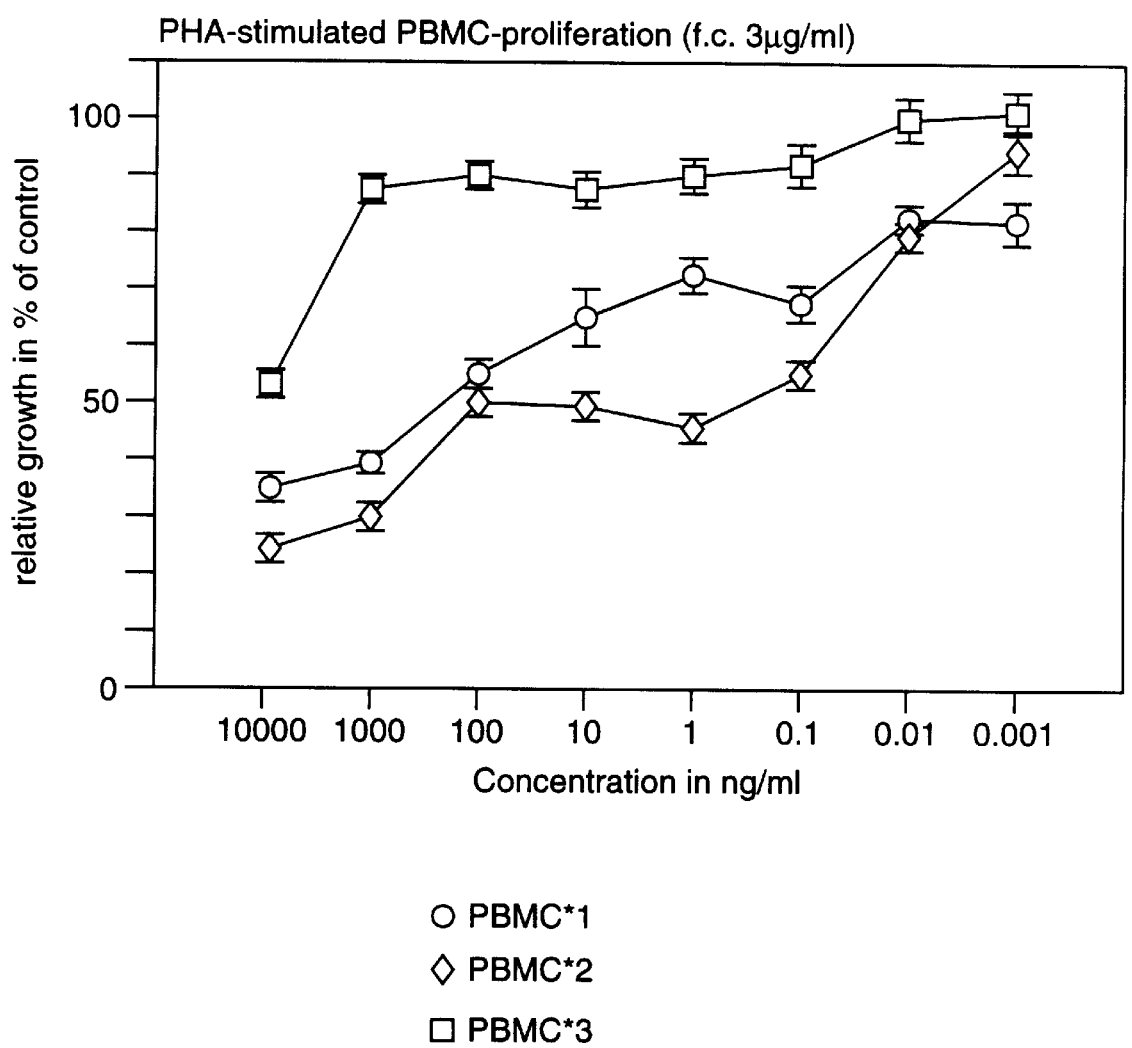
Figure 5:
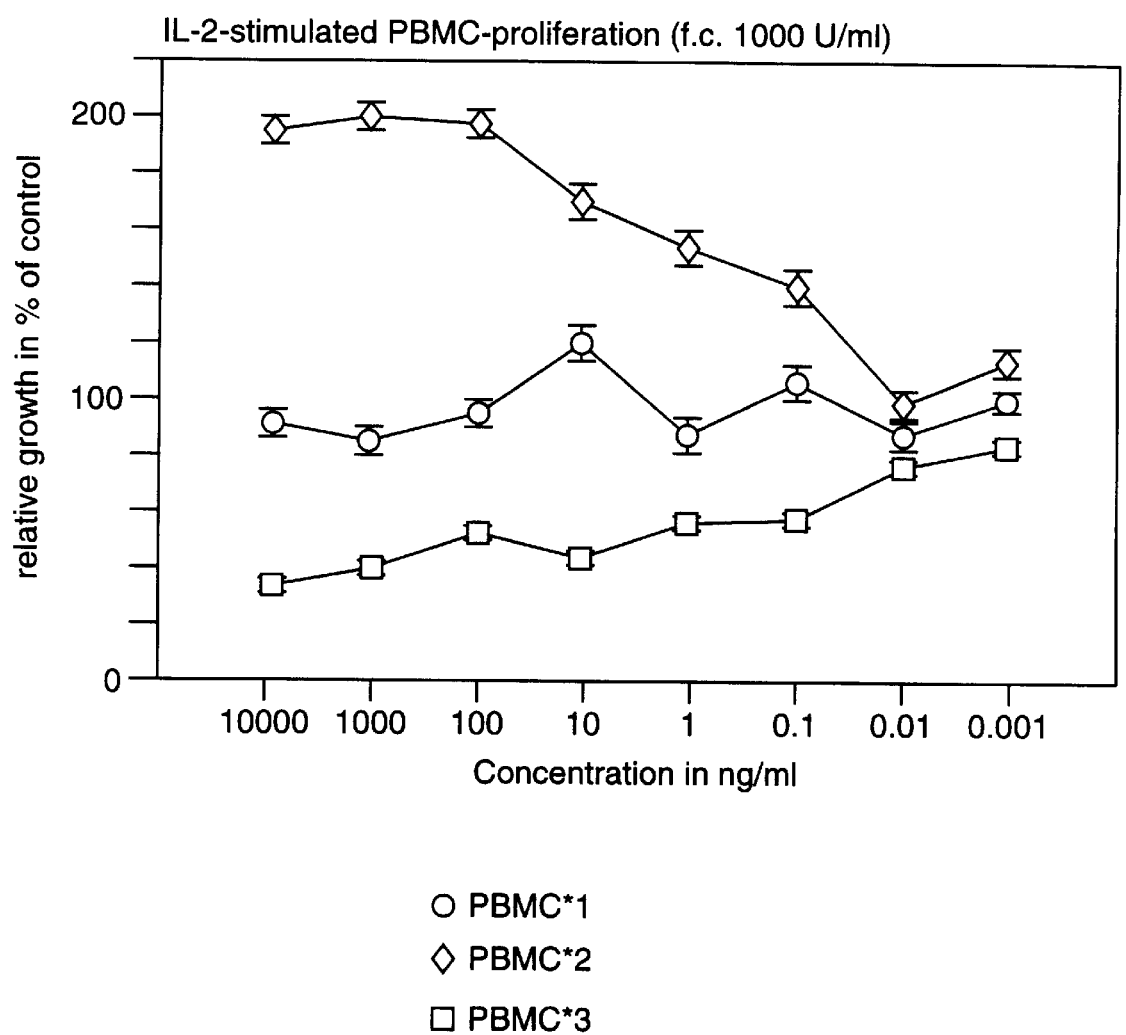

MIA inhibits IL-2 dependent and phytohaemagglutinin-dependent lymphocyte proliferation Peripheral blood lymphocytes (PBMC) can be stimulated in standardized and a classical manner using phytohaemagglutinin (PHA) and interleukin-2 (IL-2) (J. E. Coligan, A. M. Kruisbeek, D. H. Margulies, E. M. Shevach, W. Strober, Current protocols in immunology, NIH Monograph, J. Wiley Sons, New York, 1992). In this process T cells are stimulated almost exclusively with PHA and IL-2 stimulates predominantly T lymphocytes but also B cells with an IL-2 receptor. When they are co-incubated with MIA in the stated dose range (protein purity: after the first purification step (Biogel P10 column), the activity is about 50–100-fold lower than after complete purification) MIA it is possible to achieve a very strong inhibition of the PHA response (FIG. 4). The IL-2 response is inhibited in a higher dose range (FIG. 5).

EXAMPLE 5

Recombinant expression of MIA as fusion protein in *E. coli*

EXAMPLE 5a

Construction of expression vectors

Figure 6:
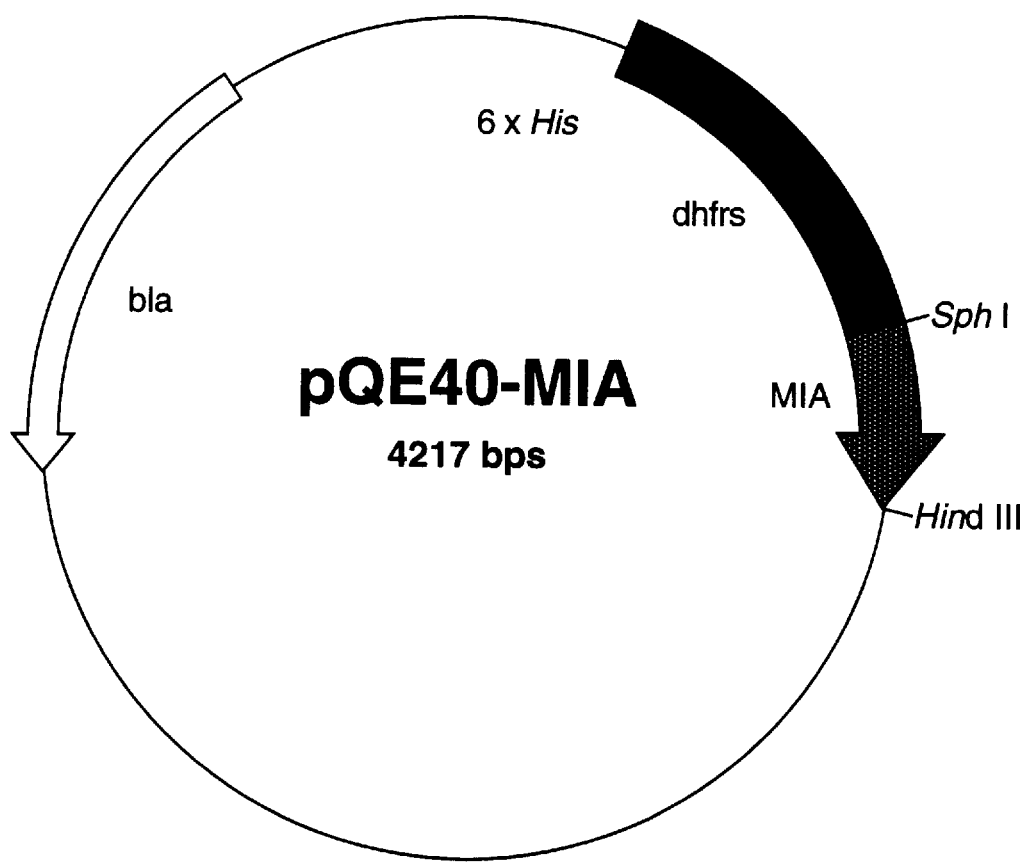

For the expression of MIA as a fusion protein with a protein suitable as a carrier in *E. coli* there may be applied, for instance, the commercially available vector pQE40 (Cat. No. 33403, DIAGEN GmbH, Düsseldorf). Into this vector a cDNA fragment coding for MIA in mature form is inserted between the restriction sites SphI and HindIII which are present once each. This type of fragment is produced most simply by PCR amplification according to the known techniques, using the cloned MIA cDNA as a matrix and two suitable primers (5'-GATGCATGCGGTCCTATGCCCAAGCTG-3' (SEQ ID NO: 9) and 5'-GATAAGCTTTCACTGGCAGTAGAAATC-3' (SEQ ID NO: 10). The PCR fragment obtained is cut with SphI and HindIII and ligated into the vector pQE40 treated in the same manner. The resulting plasmid expresses a fusion protein of DHFR (dihydrofolate reductase as carrier) and MIA. In order to enable free MIA to be cleaved proteolytically from this fusion protein, a DNA segment coding for the recognition sequence of the IgA protease (Ser Arg Pro Pro/Ser) is cloned into between DHFR and MIA. This is accomplished by opening the expression plasmid with BglII (partial restriction with subsequent isolation of the linearized vector) and SphI, followed by insertion of an adaptor (5'-GATCTAGCCGGCCGCCCAGCCCGGCATG-3' (SEQ ID NO: 11) and 5'-CCGGGCTGGGCGGCCGGCTA-3' (SEQ ID NO: 12), hybridized to double strand). The resulting expression plasmid pQE40-MIA codes for a fusion protein of DHFR and MIA, with a cleavage site for IgA protease being located between DHFR and MIA. The fusion protein carries at the N-terminus 6 histidines which can be used for purifying the fusion protein with the aid of Ni-chelate gel materials. Processes of this kind are described in EP-A 0 282 042 and EP-A 0 253 303 which are incorporated herein by reference. FIG. 6 shows the expression plasmid pQE40-MIA.

The content of MIA can be optimized by eliminating the carrier protein DHFR and replacing it by a peptide being as small as possible and fulfilling the same functions. Such suitable peptides are, for instance, MetArgGlySerHisHisHisHisHisHisGlySerSerArgProPro (SEQ ID NO: 13) (this peptide can be cleaved from the immediately following amino acid sequence of the mature MIA by IgA protease; processes of this kind are described in WO 91/11520 which is incorporated herein by reference) or MetArgGlySerHisHisHisHisHisHisGlySerValAspAspAsp-AspLys- (SEQ ID NO: 14) (this peptide can be cleaved from the immediately following amino acid sequence of the nature MIA by enterokinase). Expression plasmids which code for such MIA peptide fusions can be prepared by the following procedure: PCR amplification using MIA cDNA (SEQ ID NO:1) as a matrix and the primers 5'-AAAAAGGATCCAGCCGGCCGCCCGGTCCTATG-CCCAAGCTGGC-3' (SEQ ID NO: 15) and 5'-GGCGAGCAGCCAGATCTCCATAG-3' (SEQ ID NO: 16) yields a fragment which is recut with BamHI and BglII. The expression vector pQE40-MIA is also restricted with BamHI and BglIII; the smaller one of the resulting fragments is discarded and replaced by the described PCR fragment. Thereby an expression vector is obtained which, after induction, expresses the fusion protein MetArgGlySerHisHisHisHisHisHisGlySerSerArgProPro-MIA (SEQ ID NO: 13). The fusion protein MetArgGlySerHisHisHisHisHisHisGlySerValAspAspAsp-AspLys-MIA (SEQ ID NO: 14) is obtained in an absolutely analogous manner using the primers 5'-AAAAAA-GGATCCGTTGATGATGACGATAAAGGTCCTATGCC-CAAGCTGGC- 3' (SEQ ID NO: 17) and 5'-GGCGAGCAGCCAGATCTCCATAG-3' (SEQ ID NO: 16).

Additional similar fusion proteins of peptides and MIA can be prepared in an analogous manner and cloned under the control of suitable (preferentially strong and inducible promoters) into one of the numerous plasmids described for *E. coli*, and brought to expression. Fusion of MIA with a peptide which, in *E. coli*, leads to secretion of the fusion protein into periplasma, followed by cleavage and release of MIA, is another alternative. This process is described in WO 88/09373 which is incorporated herein by reference.

EXAMPLE 5b

Expression of fusion proteins and recovery of MIA

The expression plasmid pQE40-MIA (or a similar expression plasmid which can be obtained, for example, by using another basic vector or another carrier protein or carrier peptide; such alternatives are also described in, besides in Example 5a, Methods of Enzymology 185 (Gene Expression Technology), ed. David V. Goeddel, Academic Press 1991) is transfected into a suitable *E. coli* strain which has a sufficient expression of the lac repressor, so that an inducible expression of the MIA fusion protein can be achieved. For this purpose there is suitable, for example, the strain *E. coli* M15[pREP4] which is commercially available together with pQE40 (Diagen GmbH, Düsseldorf), or other *E. coli* strains such as, for instance, UT5600 (Earhart et al., FEMS Microbiology Letters 6 (1979) 277–280), or *E. coli* BL21 (Grodberg and Dunn, J. Bacteriol. 170 (1988) 1245–1253), which have been transfected with a lac repressor-expressing helper plasmid such as, for instance, pUBS520 (described in Brinckmann et al., Gene 85 (1989) 109–114 or in EP-B 0 373 365) beforehand. Next, MIA can be obtained by the following procedure: *E. coli* M15 [pREP4/pQE40-MIA] is cultured on LB medium until an optical density of 0.6 (measured at 550 nm) is achieved, then IPTG (isopropyl-β-D-thiolgalactopyranoside, Boehringer Mannheim GmbH) is added at a final concentration of 1 mM and subsequently cultured further for 4 hours. The cells are separated by centrifugation, placed in 100 mM sodium-phosphate buffer at pH 7.5 with 300 mM NaCl and lysed by being frozen and thawn three times and subsequently subjected to ultrasonic treatment. To the lysate clarified by centrifugation Ni-NTA-agarose (Diagen GmbH) is added, taking into account the maximum binding capacity as stated by the manufacturer, and incubated overnight at ambient temperature, while mixing. The gel material so loaded with fusion protein is separated by low-speed centrifugation, washed two times with 100 mM sodium phosphate buffer at pH 7.5 and two times with sodium phosphate buffer at pH 6.1. Thereafter, MIA is cleaved from the fusion protein by incubation of the gel material with IgA protease (Boehringer Mannheim GmbH) in 100 mM sodium phosphate buffer pH 7.5 overnight at 37° C. The gel material is separated by centrifugation overnight and the MIA-containing supernatant is employed, after sterile filtration, in the activity tests described in Examples 3 and 4.

EXAMPLE 6

Recombinant expression of fusion-free MIA in *E. coli*

The DNA sequence coding for MIA is modified in such fashion as to allow for efficient expression in *E. coli*. For this purpose PCR amplification is carried out using human MIA cDNA (SEQ ID NO:1) as a matrix and the primers 1 (5'-AAAAACATATGGGACCAATGCCAAAATTAGC-AGATCGTAAATTATGTGCAGATCAGGAG-3' (SEQ ID NO: 19)) and 2 (5'AAAAAAAGCTTTCACTGGCAGTAGAAATC-3' (SEQ ID NO: 20)). Primer 1 changes the MIA-coding sequence in the N terminal region in such fashion that, while the MIA amino acid sequence is not changed, the DNA sequence and, thus, the mRNA sequence for *E. coli* are optimized. The start codon Met is added, and at this very site a recognition sequence of the restriction endonuclease NdeI is inserted, which sequence allows for subsequent cloning of the so modified MIA-coding fragment into a vector containing a (preferentially strong and inducible) promoter and a translation initiation sequence (Shine Dalgarno sequence) with a subsequently placed NdeI cleavage site. Primer 2 acts as a 3'-counter-primer and contains a HindIII cleavage site, so as to allow for the insertion of the modified MIA-coding fragment into the vector as an NdeI HindIII fragment. The so modified MIA-coding sequence is shown in SEQ ID NO: 18. An expression plasmid prepared in this manner is p11379 (DSM 9267) which was deposited at "Deutsche Sammlung von Mikroorganismen und Zellkulturen GmbH", D-38124 Braunschweig on Jun. 29, 1994.

For expression, an expression plasmid for fusion-free MIA is transfected into a suitable *E. coli* strain. Such strains are, in the case of the use of an expression plasmid under the control of lac repressor such as the expression plasmid p11379, strains which possess a sufficiently high intracellular concentration of lac repressor. These kinds of strains can be prepared by transfection of a second plasmid such as pREP4 (Diagen GmbH), pUBS 500 or pUBS520 (Brinckmann et al., Gene 85 (1989) 109–114). The applied *E. coli* strains should preferably have a low protease activity of the cells proper, as is the case, for instance, with *E. coli* UT5600 (Earhart et al., FEMS Microbiology Letters 6 (1979) 277–280), *E. coli* BL21 (Grodberg and Dunn, J. Bacteriol. 170 (1988) 1245–1253) or *E. coli* B. Then, expression cultivation is accomplished in a fashion analogous to Example 5b. In order to recover MIA, the MIA obtained as a protein aggregate from *E. coli* is processed according to the procedures described in EP 0 241 022, EP 0 364 926, EP 0 219 874 and DE-A 40 37 196.

In detail, for example the following procedure is applied for this purpose: MIA-containing protein aggregates from *E. coli* fermentations (socalled "inclusion bodies") are solubilized in 6M guanidinium hydrochloride, 100 mM TrisHCl at pH 8, 1 mM EDTA, subsequently adjusted to a pH of 3 to 4 and dialyzed against 4M guanidinium hydrochloride at pH 3.5. The renaturing of the solubilized protein is then carried out in 1M arginine at pH 8, 1 mM EDTA, 5 mM GSH (glutathione, reduced) and 0.5 mM GSSG (glutathione, oxidized). From the renaturing preparation, MIA can be obtained, for instance, after addition of 1.4M ammonium sulfate by adsorption to hydrophobic gel matrices such as Fractogel TSK Butyl (E. Merck, Darmstadt) and subsequent elution in 20 mM TrisHCl at pH 7.

EXAMPLE 7
Recombinant expression of MIA in eukaryotic cells

EXAMPLE 7a
Recombinant expression of MIA in mammalian cells

Figure 7:
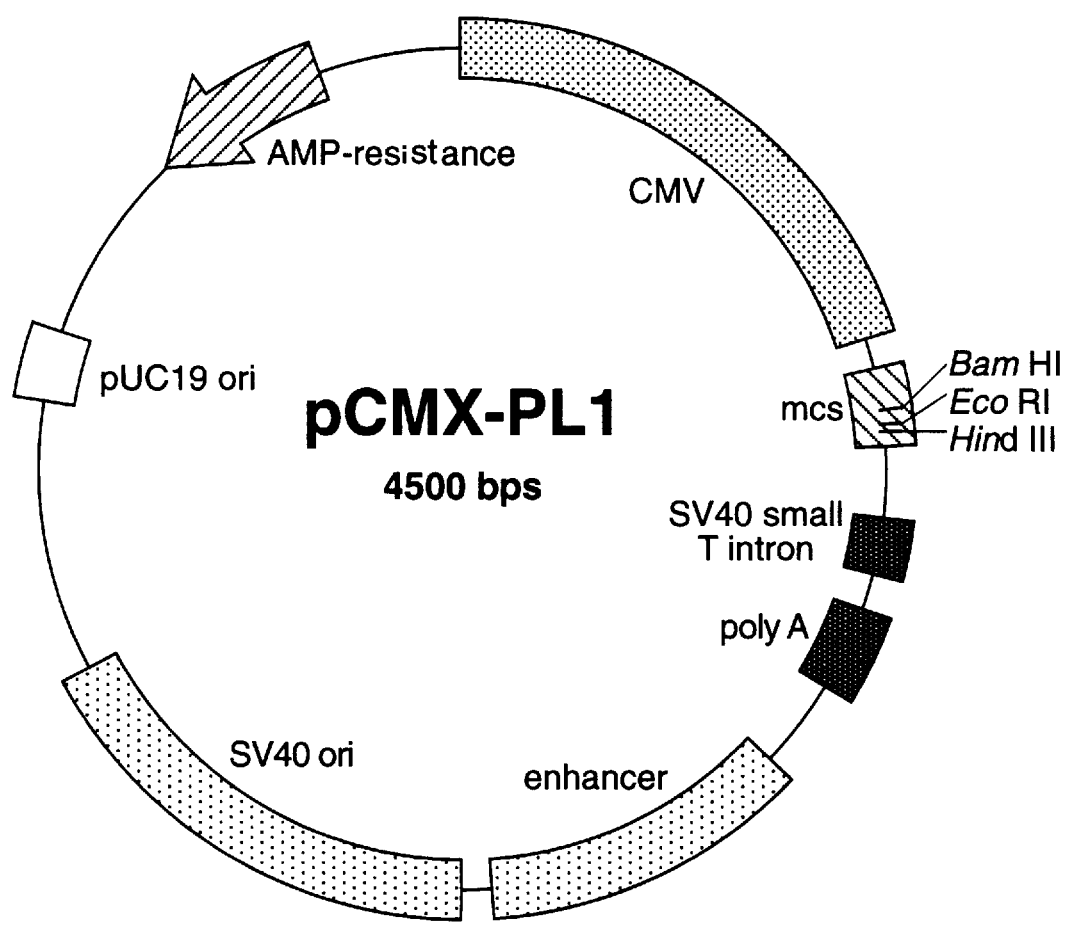

For this, the human (SEQ ID NO:1) or murine (SEQ ID NO:4) MIA cDNA or the corresponding genomic DNA segments are ligated into a vector in which they are transcribed into mammalian cells, on the basis of a strong promoter-enhancer system (in the case of the genomic MIA fragments, this step is needed because the promoters of MIA proper only are active in certain cell types, for example melanomas, and are therefore not suitable for a general recombinant expression; however, expression can also be accomplished by homologous recombination in vitro as described in example 9). Such promoters and enhancers are mostly from viruses such as SV40, hCMV, polyoma or retroviruses. As an alternative there can also be applied promoter-enhancer systems which are specific to a certain cell type or tissue type, such as, for instance, WAP-, MMTV- or immune globuline promoter, or systems which are inducible, such as, for instance, metallothioneine promoter. This kind of vector supplements the MIA cDNA (if the latter is used) with donor and acceptor signals for RNA processing as well as a signal for poly-A-addition. For example, pCMX-pL1 (Umesono et al., Cell 65 (1991) 1255–1266) which is shown in FIG. 7 is such a suitable vector. Into the one and only EcoRI cleavage site of this vector the MIA cDNA provided with EcoRI linkers is ligated, wherein it is ensured by restriction analysis with the aid of the other cleavage sites in the polylinker of this vector (see SEQ ID NO: 23) that the MIA cDNA is oriented in reading direction of the CMV promoter. An absolutely analogous procedure is applied when cloning into other vectors, e.g. into pCDNA3 (Invitrogen, San Diego/USA) or pSG5 (Stratagene, LaJolla/USA). The DNA of the so obtained expression plasmids is prepared from *E. coli* and transfected into the mammalian cells, applying techniques that are specific to the cell types in the particular case (Methods of Enzymology 185 (Gene Expression Technology), ed. David V. Goeddel, Academic Press 1991, section V). The expression plasmid pCMX-pL1-MIA is transfected into the human teratocarcinoma line PA-1sc9177 (Büttner et al., Mol. Cell. Biol. 11 (1991) 3573–3583) according to methods that have been described (Büttner et al., Mol. Cell. Biol. 13 (1993) 4174–4185), wherein 200,000 cells per 100 mm culture dish are transfected with 5 µg DNA. After transfection, the cells are cultured in MEM (Gibco) without addition of fetal calf serum, whereby MIA is detectible in the cell culture supernatant after 48 hours.

EXAMPLE 7b
Recombinant expression of MIA in insect cells

For expression in insect cells, a DNA segment coding for MIA, preferably the human MIA cDNA (SEQ ID NO:1), is inserted into vectors derived from AcMNPV (Autographa californica nuclear polyhedrosis virus) or BmNPV (Bombyx mori nuclear polyhedrosis virus). For this purpose the MIA cDNA is first of all brought under the control of a strong promoter which is suitable for insect cells (D. R. O'Reilly, L. K. Miller and V. A. Luckow, Baculovirus Expression Vectors—A Laboratory Manual (1992), W. H. Freeman & Co., New York), such as the polH promoter or the p10 promoter. In order to express MIA with the help of the polH promoter the following procedure is applied: A DNA fragment coding for MIA and having cleavage sites for the restriction endonucleases EcoRI (adjacent to the 5' end of the later MIA transcript) and PstI (adjacent to the 3' end of the later MIA transcript) is obtained by PCR amplification according to known techniques and with the use of the MIA cDNA as a matrix and the primers 5'-CGTGAATTCAACATGGCCCGGTCCCTGGTGTGC-3' (SEQ ID NO: 21) and 5'-TATCTGCAGTCACTGGCAGTAGAAATCCCA-3' (SEQ ID NO: 22). This fragment is recut with EcoRI and PstI (in order to generate the corresponding cohesive ends) and ligated into the transfer vector pVL 1393 which has been restricted with the same endonucleases (D. R. O'Reilly, L. K. Miller and V. A. Luckow, Baculovirus Expression Vectors—A Laboratory Manual (1992), W. H. Freeman & Co., New York) and is commercially available (PharMingen, San Diego, Calif., or Invitrogen Corporation, San Diego, Calif.). The resulting transfer expression plasmid pVL 1393-MIA, for proliferation, is transfected into E. coli K12 and plasmid DNA is prepared according to the established methods. The transfer of the MIA DNA, which is under the control of the poIH promoter, from the transfer plasmid into the baculovirus vector is accomplished by homologous recombination according to the established methods (O'Reilly et al. (1992), see supra). For this purpose, 0.5 µg Baculo Gold DNA (linearized AcNPV virus DNA with lethal deletion and lacZ expression controlled by the poIH promoter, commercially available from PharMingen, Order No. 21100D) and 2 µg pVL13-93-MIA are mixed, incubated at ambient temperature for 5 minutes and subsequently mixed with 1 ml 125 mM Hepes at pH 7.1, 125 mM $CaCl_2$, 140 mM NaCl. This mixture is added to $2 \times 10^6$ SF9 insect cells (Invitrogen, Order No. B825-01) in a culture dish of a diameter of 60 mm which was coated with 1 ml Grace's Medium with 10% fetal calf serum beforehand. After 4 hours of incubation at 4° C. the DNA-containing medium is removed and the cells are incubated in fresh medium at 27° C. for a period of 4 days. The recombinant baculoviruses obtained in this manner are subsequently purified two times via plaque formation (O'Reilly et al. (1992), see supra), wherein viruses which have inserted MIA by homologous recombination are distinguished from the employed wild type viruses (AcNPV with lethal deletion and lacZ expression controlled by the poIH promoter, commercially available from PharMingen, Order No. 21100D) by the absence of β-galactosidase activity (optically recognizable by the absence of blue colour in the presence of 5-bromo-4-chloro-3-indolyl-β-D-galactopyranoside). With a so obtained MIA-expressing recombinant baculovirus SF9 cells are infected (MOI=20 pfu/cell) according to the established methods (O'Reilly et al. (1992), see supra) and incubated further for at least 36 hours at 27° C. in serum-free medium (Cell/Perfect Bac serum free insect cell culture medium, Stratagene, Order No. 205120). Subsequently the cell culture supernatants are removed, viruses contained in the supernatant are separated by ultracentrifugation (Beckmann Ti 60 Rotor, 30,000 rpm) and thereafter the supernatant is filtered through a Microcon 100 Filter (Amicon, exclusion limit 100 kD). The so obtained MIA-containing solution can be used in the tests described in Examples 3 and 4, or can be purified further in accordance with Example 1.

EXAMPLE 8
Detection of MIA mRNA in various cells

The detection of expression of MIA in a particular cell and, thus, of the presence of MIA mRNA, can be accomplished, on the one hand, with the established methods of nucleic acid hybridization such as, for instance, Northern hybridization, in situ hybridization, dot or slot hybridization, and diagnostic techniques derived therefrom (Sambrook et al., Molecular Cloning—A Laboratory Manual (1989), Cold Spring Harbor Laboratory Press; Nucleid Acid Hybridisation—A Practical Approach (1985), eds. B. D. Hames and S. J. Higgins, IRL Press; WO 89/06698, EP-A 0 200 362, U.S. Pat. No. 2,915,082, EP-A 0 063 879, EP-A 0 173 251, EP-A 0 128 018). On the other hand, there may be applied methods from the large variety of amplification techniques, using MIA specific primers (PCR Protocols—A Guide to Methods and Applications (1990), eds. M. A. Innis, D. H. Gelfand, J. J. Sninsky, T. J. White, Academic Press Inc; PCR—A Practical Approach (1991), eds. M. J. McPherson, P. Quirke, G. R. Taylor (1991), IRL Press). Tables 2A and 2B show MIA expression in various human tumours, tumour lines and normal cells, which was determined in this case by Northern hybridization using the radiolabelled human MIA cDNA (SEQ ID NO:1). For this purpose the RNA was isolated from the listed cells according to the method of Chomczynski and Sacchi, Anal. Biochem. 162 (1987) 156–159. 20 µg total RNA were separated on a 1% agarose formaldehyde gel and transferred to nylon membranes (Amersham, Braunschweig) according to standard methods (Sambrook et al., Molecular Cloning—A Laboratory Manual (1989), Cold Spring Harbor Laboratory Press). As a sample, the complete human MIA cDNA (SEQ ID NO:1) was radiolabelled (Feinberg and Vogelstein, Anal. Biochem. 137 (1984) 266–267). Hybridization was carried out at 68° C. in 5×SSC, 5×Denhardt's, 0.5% SDS, 10% dextran sulfate and 100 µg/ml salmon sperm DNA. Thereafter the membranes were washed two times per hour in 1×SSC at 68° C. and then exposed to X-ray film.

TABLE 2A

| Tumour | Number tested | Positive at Northern Blotting |
| --- | --- | --- |
| Astrocytoma | 10 | 3 |
| Oligodendroglioma | 4 | 0 |
| Ependymoma | 3 | 0 |
| Neuroblastoma | 4 | 0 |
| Glioblastoma | 13 | 0 |
| Colon CA | 2 | 1 |
| Malignant melanoma CNS metastasis | 6 | 6 |
| Medulloblastoma | 2 | 0 |
| carcinoma of the breast | 1 | 0 |
| bronchial carcinoma CNS metastasis | 2 | 0 |

TABLE 2B

| Normal cells | Number tested | Positive at Northern Blotting |
| --- | --- | --- |
| Embryonic fibroblasts | 2 | 0 |
| mononucleic blood cells (3 donours) | 3 | 0 |

EXAMPLE 9
Use of MIA coding nucleic acids for therapeutic purposes

MIA inhibits the proliferation and metastasising of tumour cells. In an animal model or a patient this effect may be caused not only by exogenous introduction of MIA protein but also by insertion of a DNA segment which either codes for MIA under a suitable promoter or contains a suitable promoter capable of integrating before the cell's own MIA gene into the genome by homologous recombination. In the latter case, this promoter must be flanked by sequence portions which are to the highest possible extent homologous, or preferably even identical, to the sequences of the human (or, in the case of an animal model, animal) MIA gene in the 5'-untranslated region (see e.g. WO 91/09955). By this process it is possible to achieve that the tumour cell is expressing MIA to an increased extent and, thus, inhibits its own proliferation and metastasising if the DNA segments are inserted in the tumour cell proper. In many cases, however, the corresponding gene segment will not need to be inserted specifically and exclusively into the tumour cells proper, because also an expression in other body cells, preferably adjacent to the tumour, will bring about inhibition of the tumour cells through increased MIA release. The following example shows the therapeutic effect of a MIA-coding DNA segment in an animal model.

The injection of murine B16 melanoma cells (ATCC CRL 6322) into the caudal vene of C57BL mice, followed by quantification of lung metastases, is an established in vivo model of metastasis formation. 100,000 cells of the melanoma line B16 were injected behind the eyeballs of C57BL mice (day 1: 16 animals). After 48 hours, in 8 animals, 100 µg of the MIA expression plasmid pCMX-PL1-MIA (Example 7a) in TE (10 mM TrisCl pH 8.0, 1 mM EDTA), mixed with DOTAP transfection reagent (Leventis and Silvius, Biochim. Biophys. Acta 1023 (1990) 124–132, commercially available from Boehringer Mannheim GmbH, Cat. No. 1202375), were injected in each case into the caudal vene. The control group (8 animals) was given the same plasmid, however without MIA sequences. After 13 days, 6 of 8 animals from the control group without MIA had developed a local tumour; the average number of metastases in the lung, spleen, kidney and liver was 7.8. In the group which had been given the MIA coding plasmid, only 4 of 8 animals developed a local tumour and the average number of metastases was 2.7.

We claim:

1. An isolated nucleic acid molecule, the complementary sequence of which hybridizes to SEQ ID NO: 1 or SEQ ID NO: 3, at 55°–66° C., 6×SSC, 5×Denhardt's solution, 100 ug/ml salmon sperm DNA or 68° C., 5×SSC, 5×Denhardt's solution, 0.5% SDS, 10% dextran sulfate and 100 ug/ml salmon sperm DNA.

2. The isolated nucleic acid molecule of claim 1, which encodes a protein having melanoma inhibiting activity, and which inhibits growth of cell lines HTZ 19dM and ATCC CRL 1424.

3. The isolated nucleic acid molecule of claim 2, which encodes a protein having the amino acid sequence of SEQ ID NO: 2.

4. The isolated nucleic acid molecule of claim 2, which encodes a protein having an amino acid sequence comprising amino acids 1 through 107 of SEQ ID NO: 2.

5. The isolated nucleic acid molecule of claim 2, having the nucleotide sequence set forth in SEQ ID NO: 1, SEQ ID NO: 3, or SEQ ID NO: 4.

6. A recombinant expression vector comprising the isolated nucleic acid molecule of claim 2, operably linked to a promoter.

7. A recombinant cell comprising the isolated nucleic acid molecule of claim 2.

8. The recombinant cell of claim 7, wherein said cell is a prokaryotic cell.

9. The recombinant cell of claim 7, wherein said cell is a eukaryotic cell.

10. The recombinant cell of claim 8, wherein said prokaryotic cell is an *E. coli* cell.

11. The recombinant cell of claim 9, wherein said eukaryotic cell is a mammalian cell.

12. A process for recombinant production of a protein which has melanoma inhibiting activity and which inhibits growth of cell lines HTZ 19-dM and ATCC-CRL 1424, comprising transforming or transfecting a cell with the isolated nucleic acid molecule of claim 2, to produce said protein and isolating said protein from said cell.

13. The process of claim 12, wherein said isolated nucleic acid molecule has a nucleotide sequence selected from the group consisting of SEQ ID NO: 1, SEQ ID NO: 3, and SEQ ID NO: 4.

14. A method for detecting a nucleic acid molecule which encodes a protein having melanoma inhibiting activity, comprising incubating a sample with the isolated nucleic acid molecule of claim 2 and determining any hybridization of said isolated nucleic acid molecule to a target nucleic acid molecule as a determination of presence of a nucleic acid molecule which encodes a protein having melanoma inhibiting activity.

15. The method of claim 14, further comprising amplifying said target nucleic acid molecule prior to detecting it.

16. A method for producing a protein which has melanoma inhibiting activity and which inhibits growth of cell lines HTZ 19-dM and ATCC 1424, comprising:
homologously recombining a DNA construct into a genome of a cell which comprises an endogenous gene for said protein, said DNA construct comprising a regulatory element which is capable of stimulating expression of said endogenous gene when operably linked thereto, and at least one DNA targeting segment having a nucleotide sequence homologous to a region within or proximal to said endogenous gene, culturing said cell to produce said protein, and recovering said protein.

17. A process for producing a protein which has melanoma inhibiting activity and which inhibits growth of cell lines HTZ 19-dM and ATCC 1424, comprising:
homologously recombining a DNA construct into a genome of a mammalian cell, said DNA construct comprising:
(a) a nucleic acid molecule which encodes said protein,
(b) a DNA regulatory element capable of stimulating expression of (a), and
(c) at least one DNA target segment homologous to a region of said genome; culturing said mammalian cells following said homologous recombination protein, and recovering said protein.

18. An isolated protein which has melanoma inhibiting activity and which inhibits growth of cell lines HTZ 19-dM and ATCC CRL 1424, which is encoded by
(a) a nucleic acid molecule having the nucleotide sequence set forth in SEQ ID NO: 1,
(b) a nucleic acid molecule having the nucleotide sequence set forth in SEQ ID NO: 3,
(c) a nucleic acid molecule comprising nucleotides 112–432 of SEQ ID NO: 1,
(d) a nucleic acid molecule comprising nucleotides 40–432 of SEQ ID NO: 1,
(e) a nucleic acid molecule having the nucleotide sequence set forth in SEQ ID NO: 4,
(f) a nucleic acid molecule comprising nucleotides 112–494 of SEQ ID NO: 4,
(g) a nucleic acid molecule comprising nucleotides 179–499 of SEQ ID NO: 4,
(h) a nucleic acid molecule, which encodes a protein having an amino acid sequence identical to the amino acid sequence of a protein expressed by any of (a), (b), (c), (d), (e), (f) or (g).

19. The isolated protein of claim 18, having a molecular weight to about 11 kilodaltons as determined by SDS-PAGE, under non-reducing conditions.

20. The isolated protein of claim 19, obtained from cell culture supernatant of cell line HTZ 19dM via gel chromatography and reversed phase, high performance liquid chromatography.

21. The isolated protein of claim 18, having an amino acid sequence identical to the amino acid sequence encoded by nucleotides 40–432 or 112–432 of SEQ ID NO: 1.

22. The isolated protein of claim 18, having an amino acid sequence identical to the amino acid sequence encoded by nucleotides 110–499 or 179–499 of SEQ ID NO: 4.

23. Isolated cell line HTZ 19-dM (DSM ATCC 2133).

24. Antibody which specifically binds to the protein of claim 18 obtained by immunizing an animal with said protein and isolating an antibody produced by said animal in response to said protein.

25. A process for making an antibody which binds with the protein of claim 18, comprising immunizing a subject animal with said protein and recovering any antibodies produced in response thereto.

26. Process for making a therapeutic agent useful in tumor therapy comprising combining the protein of claim 18 with a pharmaceutical auxiliary substance, a filler, or an additive.

27. Therapeutic composition comprising the isolated protein of claim 18 and a pharmaceutical auxiliary substance, a filler, or an additive.

* * * * *

SEQUENCE LISTING ( 1 ) GENERAL INFORMATION:

( i i i ) NUMBER OF SEQUENCES: 24

( 2 ) INFORMATION FOR SEQ ID NO: 1:

( i ) SEQUENCE CHARACTERISTICS:
( A ) LENGTH: 459 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 40..432

( i x ) FEATURE:
( A ) NAME/KEY: sig_peptide
( B ) LOCATION: 40..111

( i x ) FEATURE:
( A ) NAME/KEY: mat_peptide
( B ) LOCATION: 112..432

( x i ) SEQUENCE DESCRIPTION: SEQ ID NO: 1:

```
CCAGCACCCC  CTTGCTCACT  CTCTTGCTCA  CAGTCCACG  ATG  GCC  CGG  TCC  CTG              54
                                               Met  Ala  Arg  Ser  Leu
                                               - 24                - 20

GTG  TGC  CTT  GGT  GTC  ATC  ATC  TTG  CTG  TCT  GCC  TTC  TCC  GGA  CCT  GGT     102
Val  Cys  Leu  Gly  Val  Ile  Ile  Leu  Leu  Ser  Ala  Phe  Ser  Gly  Pro  Gly
               - 15                     - 10                          - 5

GTC  AGG  GGT  GGT  CCT  ATG  CCC  AAG  CTG  GCT  GAC  CGG  AAG  CTG  TGT  GCG     150
Val  Arg  Gly  Gly  Pro  Met  Pro  Lys  Leu  Ala  Asp  Arg  Lys  Leu  Cys  Ala
               1                   5                         10

GAC  CAG  GAG  TGC  AGC  CAC  CCT  ATC  TCC  ATG  GCT  GTG  GCC  CTT  CAG  GAC     198
Asp  Gln  Glu  Cys  Ser  His  Pro  Ile  Ser  Met  Ala  Val  Ala  Leu  Gln  Asp
     15                       20                           25

TAC  ATG  GCC  CCC  GAC  TGC  CGA  TTC  CTG  ACC  ATT  CAC  CGG  GGC  CAA  GTG     246
Tyr  Met  Ala  Pro  Asp  Cys  Arg  Phe  Leu  Thr  Ile  His  Arg  Gly  Gln  Val
30                       35                      40                         45

GTG  TAT  GTC  TTC  TCC  AAG  CTG  AAG  GGC  CGT  GGG  CGG  CTC  TTC  TGG  GGA     294
Val  Tyr  Val  Phe  Ser  Lys  Leu  Lys  Gly  Arg  Gly  Arg  Leu  Phe  Trp  Gly
                    50                           55                         60

GGC  AGC  GTT  CAG  GGA  GAT  TAC  TAT  GGA  GAT  CTG  GCT  GCT  CGC  CTG  GGC     342
Gly  Ser  Val  Gln  Gly  Asp  Tyr  Tyr  Gly  Asp  Leu  Ala  Ala  Arg  Leu  Gly
               65                         70                         75
```

| TAT | TTC | CCC | AGT | AGC | ATT | GTC | CGA | GAG | GAC | CAG | ACC | CTG | AAA | CCT | GGC | 390 |
| Tyr | Phe | Pro | Ser | Ser | Ile | Val | Arg | Glu | Asp | Gln | Thr | Leu | Lys | Pro | Gly | |
| | | 80 | | | | | 85 | | | | | 90 | | | | |

| AAA | GTC | GAT | GTG | AAG | ACA | GAC | AAA | TGG | GAT | TTC | TAC | TGC | CAG | | | 432 |
| Lys | Val | Asp | Val | Lys | Thr | Asp | Lys | Trp | Asp | Phe | Tyr | Cys | Gln | | | |
| | 95 | | | | | 100 | | | | | 105 | | | | | |

TGAGCTCAGC CTACCGCTGG CCCTGCC  459

(2) INFORMATION FOR SEQ ID NO: 2:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO: 2:

| Met | Ala | Arg | Ser | Leu | Val | Cys | Leu | Gly | Val | Ile | Ile | Leu | Leu | Ser | Ala |
| -24 | | | | -20 | | | | | -15 | | | | | -10 | |

| Phe | Ser | Gly | Pro | Gly | Val | Arg | Gly | Gly | Pro | Met | Pro | Lys | Leu | Ala | Asp |
| | | | -5 | | | | | 1 | | | | 5 | | | |

| Arg | Lys | Leu | Cys | Ala | Asp | Gln | Glu | Cys | Ser | His | Pro | Ile | Ser | Met | Ala |
| | 10 | | | | | 15 | | | | | 20 | | | | |

| Val | Ala | Leu | Gln | Asp | Tyr | Met | Ala | Pro | Asp | Cys | Arg | Phe | Leu | Thr | Ile |
| 25 | | | | | 30 | | | | | 35 | | | | | 40 |

| His | Arg | Gly | Gln | Val | Val | Tyr | Val | Phe | Ser | Lys | Leu | Lys | Gly | Arg | Gly |
| | | | | 45 | | | | | 50 | | | | | 55 | |

| Arg | Leu | Phe | Trp | Gly | Gly | Ser | Val | Gln | Gly | Asp | Tyr | Tyr | Gly | Asp | Leu |
| | | | 60 | | | | | 65 | | | | | 70 | | |

| Ala | Ala | Arg | Leu | Gly | Tyr | Phe | Pro | Ser | Ser | Ile | Val | Arg | Glu | Asp | Gln |
| | | 75 | | | | | 80 | | | | | 85 | | | |

| Thr | Leu | Lys | Pro | Gly | Lys | Val | Asp | Val | Lys | Thr | Asp | Lys | Trp | Asp | Phe |
| | 90 | | | | | 95 | | | | | 100 | | | | |

| Tyr | Cys | Gln |
| 105 | | |

(2) INFORMATION FOR SEQ ID NO: 3:

(i) SEQUENCE CHARACTERISTICS:
        (A) LENGTH: 3565 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: sig_peptide
        (B) LOCATION: 1378..1449

(ix) FEATURE:
        (A) NAME/KEY: exon
        (B) LOCATION: 1378..1504

(ix) FEATURE:
        (A) NAME/KEY: exon
        (B) LOCATION: 1586..1719

(ix) FEATURE:
        (A) NAME/KEY: exon
        (B) LOCATION: 2804..2914

(ix) FEATURE:
        (A) NAME/KEY: exon
        (B) LOCATION: 3232..3252

(ix) FEATURE:
  (A) NAME/KEY: -
  (B) LOCATION: one-of(2216)
  (D) OTHER INFORMATION: /note= "N in position 2216 denotes an indefinite number ans sequence of nucleotides"

(xi) SEQUENCE DESCRIPTION: SEQ ID NO: 3:

| | | | | | | |
|---|---|---|---|---|---|---|
| TCTAGACANA | TAAAAATAAA | AGAAATCATC | CAAGAATGGT | GACTTGCCTA | CTATTCTACT | 60 |
| CGAGAGGCTG | AGAGGGAGG | ATTTCTTGAC | CCCGGNAGTT | TAAGGATGCA | GTGAGCTATG | 120 |
| ATCACATCAC | TGTACTTCAG | CCTGAGCAAC | AGCAAGATCC | TGTCTCTAAA | AATTAAATAA | 180 |
| GGCTGGGCTT | GGTGGCTCAT | GCTGTAATCC | CAGCACTTTG | GAAGGCCATG | GTGGGCAGAT | 240 |
| TGCTTGAGCC | CAGGAGTTTG | AGACGAGGCT | GGGCAACATG | ACGAAACCCC | GGCTCTACCA | 300 |
| AAAATACAA | AAAATTAACT | GGGCATAATG | GTACATGTCT | GTGGTCCCAG | CTACTCGGTA | 360 |
| GGCTGAGGTG | GGAGGAATGC | TTGAGCCCAG | GAAATAGGGG | CTACAGTGAA | CCAGGATGAT | 420 |
| GCCAGTGCAC | TCCAACCTGG | GCAACAGAGC | AAGACTCTAC | CTCAAAATAA | TTTAAAAAAA | 480 |
| TGGATTAATT | GGGCATAGGT | GGCTTGTGCC | TGTAGTCCCA | GTTACTCAGG | AGCCTGAGGT | 540 |
| GGGAGGATTG | CCTGAGTCTA | GGAGGTTGAG | GCTGCAGTGA | GCCGGGATGG | CACCATTGCA | 600 |
| CTCCACCTGG | GCAACAGGGT | GAGACCCTGT | CTCAAAAAG | AAAAAAAAGG | GAGGGGTTAT | 660 |
| AATCACTCCT | CCTGACATGA | TACAGAGTAT | CCATTTGAGT | TCATAACATA | AATATGTACT | 720 |
| TGGTGAATGC | TCTGTAACTA | TTGGTGAATG | CTCTGTAACT | ATTGGCTTTT | TTATTGTTCC | 780 |
| CATTTTACAT | ATAAGGAAGC | TGAGGCTTTG | TGAGGAGAAA | TAGCTTAGCC | CAGGTCATCC | 840 |
| AGTGGGAAGC | GTCTGGTGCA | GAGGAATAGT | GATCAGGGTG | GGACTTTGCC | TAGCCTAAGG | 900 |
| TTCAGCATAC | AATATTCAGT | CAGTACTCAA | GGGCTGGGCT | GTTTCTGGTA | ATCAAAGGGC | 960 |
| CTGCCTTGTC | CTCCTCCCCC | ACAGCAGGAA | ATTCCAAGGT | GGTTTTCTTT | ACAGGCTCCT | 1020 |
| CCGCTTCTGT | GGCCAGAGGG | GACAGCGGAG | GACCCCAGGT | ACCTAAGCCA | ACTCAAGAGA | 1080 |
| AGATGGAATT | GAATATTTCA | ACCACCTTAT | CTAGGCCTCT | GTGATTGTTG | AGGAGGGGC | 1140 |
| TGTCACTGGG | AAAGTTGTGA | GCTGCTTTGG | ACCTTATCTG | GGAATTTCCT | TGGGCCTTAC | 1200 |
| AGCTTTACCC | TATCCTTGAA | ATGGTTCTGG | TTTCATAGCA | ACTTCTAGGT | GGTGTGGGCG | 1260 |
| AAGTTTGGGA | CTGGTTTAGG | GCGGGACAA | GACCAAGAAC | ACAAGTTTCC | TTGTACGGGA | 1320 |
| GAGAGGAAAT | TGGAGACCCC | AGCACCCCCT | TGCTCACTCT | CTTGCTCACA | GTCCACGATG | 1380 |
| GCCCGGTCCC | TGGTGTGCCT | TGGTGTCATC | ATCTTGCTGT | CTGCCTTCTC | CGGACCTGGT | 1440 |
| GTCAGGGGTG | GTCCTATGCC | CAAGCTGGCT | GACCGGAAGC | TGTGTGCGGA | CCAGGAGTGC | 1500 |
| AGCCGTAAGA | ATGGGGAGGG | GTAGAATTGG | GCTTGGGTGT | TAGCCTGTGT | GGATGTGCTG | 1560 |
| CATTCCCCTT | CTATTCCTTC | CCTAGACCCT | ATCTCCATGG | CTGTGGCCCT | TCAGGACTAC | 1620 |
| ATGGCCCCG | ACTGCCGATT | CCTGACCATT | CACCGGGGCC | AAGTGGTGTA | TGTCTTCTCC | 1680 |
| AAGCTGAAGG | GCCGTGGGCG | GCTCTTCTGG | GGAGGCAGCG | TGCGTCTTGG | GAGAGTGAAA | 1740 |
| GAGGGAAGGG | TACAGAGCTG | GGGTAGACTC | ATTATCCCCA | TGAAGGGAAG | ATTTGAGGGG | 1800 |
| GGTGAACTGA | AATAGACATT | GTGGGGGAT | ATTGTTACTT | ACTTTATTTT | ATTTGCTTAT | 1860 |
| TATTTTTTAA | TTTTTTCCGA | GACAGAGTCT | TGCTCTGTCA | CCCAGGCTGG | ATGCAATGGC | 1920 |
| ACGATCTCGG | CTCACTGTAA | CCTCCACCTC | TTGGGTTTAA | GCGATTCTCC | AGCCTCAGCC | 1980 |
| TCCCAAGTAC | CTGGGATTAC | AGGCATGCAC | CACCACACCT | NNTAATTTTT | GTATTTTAG | 2040 |
| TAGAGACAGG | GTTTTACCAT | ATTGGCCAGG | CTGGTCTTGA | ACTCCTGACC | TCATGATCTG | 2100 |
| CCCGCCTTGG | CTCCCGGAGT | GCTGGGATTA | CAGGTGTGAG | CCACTGGCCC | CCCAGCCTAT | 2160 |

| | | | | | | |
|---|---|---|---|---|---|---|
| TTTCACTTTA | TTTACCAATT | TTAGGACCTG | ATATGGTCCC | ANNNTCTGTT | CTAGANTCTA | 2220 |
| GACACCAAGA | TACAACAACA | AATGATCCTT | TTTATTCTAA | TGGAGGGAAA | TGAACAAAAA | 2280 |
| GCAAGGCATA | AAAAATAGCA | GCAGCCGGGC | ACAGTAGCTC | ACACCTGTAA | TCCCAAGTAA | 2340 |
| GGCCAAGTNN | GGAGGATAGC | TTGAGCCCAG | GAGTTCGAGA | CCAGCCTGGG | CAACATAGCA | 2400 |
| AGACCCCCAT | CTCTATAAAA | AAAATTTAA | AATTAACTGG | GCATCATGGC | ATGTGTCTGT | 2460 |
| GGTCCCGGCT | ACTCGGGAGG | CTGAGGTGGG | AGGATTGCTT | GATCCCAGAA | GTTGAGGCTG | 2520 |
| CAGTGAGCCG | TGATCATGCT | ACTGCACCTC | AACCTGGCCG | ACACAATGAG | ACCCTGTTTC | 2580 |
| CAAAATAATA | ATAATAAAAG | CAAATATGCG | CTGCTGTGAG | AATTAACAGA | GACTTACTTG | 2640 |
| GGTGTTCAGA | AAGGGCCTCT | GAACAGGTGG | CATTTAAGCT | GAGATTCATA | TGACAAGGAT | 2700 |
| GGAGCAGTTA | TGTGGAGATC | AGGGAGAGGG | GAGAATGCAA | AGGCCTTCAG | CAGGCACAAG | 2760 |
| CTTGCCATCT | TCCAGACCCT | AGCTTTTAAC | TCCTCTTCCC | CAGGTTCAGG | GAGATTACTA | 2820 |
| TGGAGATCTG | GCTGCTCGCC | TGGGCTATTT | CCCCAGTAGC | ATTGTCCGAG | AGGACCAGAC | 2880 |
| CCTGAAACCT | GGCAAAGTCG | ATGTGAAGAC | AGACGTGAGT | GTCATGGGGG | CTGGCAAGAA | 2940 |
| ATGTGGGGGG | AGGACCCTTA | GGTTGTGGGG | ATGGGCAAAA | ATGCTCCCAC | ACTTGGCTCC | 3000 |
| CTGGCCGCCT | AGGTATGTGC | GCTGGGAGAA | ATTCTTTCCC | TGCCTCAATT | TTCTCACCAG | 3060 |
| TAAAATGGGT | CCAGTTGGGA | GGTGCAAAGA | TTAGAGGGCT | CTAGGCTAAT | TTGCATAGCA | 3120 |
| NNTGTGTGGC | CAGACCTGGG | CCCTGCAGCT | GCAGCCTTTG | CTAAAACCAC | TAGATCCTTT | 3180 |
| GTGGTGTGAC | CGCTGGTTTT | CTTTCCACTG | TTTCCCCTTT | CTCTTTTCA | GAAATGGGAT | 3240 |
| TTCTACTGCC | AGTGAGCTCA | GCCTACCGCT | GGCCCTGCCG | TTTCCCCTCC | TTGGGTTTAT | 3300 |
| GCAAATACAA | TCAGCCCAGT | GCAAACGGCT | CGTCTCCGTG | GTCTTTGGGG | TGGGGTAGGG | 3360 |
| TAGGGTGGGG | ACTGTACAAA | TGAAATGTTT | CTCTAGGTTG | CTGAATCTAA | CCAATTAACC | 3420 |
| CGCTGCCTGT | GGTAACGTCA | GTGGTTGCTA | GGCAGAGTTT | CGCTGATGAA | AGCCCTGTGC | 3480 |
| AGTAGGAGCG | CTCCTAAGCT | TAGGTTTCGA | CACAAGCAAA | GAAAACCTAA | GCAGCCCAAC | 3540 |
| TAGGGATTGT | AGTGTCCTCT | CTAGA | | | | 3565 |

( 2 ) INFORMATION FOR SEQ ID NO: 4:

( i ) SEQUENCE CHARACTERISTICS:
        ( A ) LENGTH: 581 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 110..499

( i x ) FEATURE:
        ( A ) NAME/KEY: sig_peptide
        ( B ) LOCATION: 110..178

( i x ) FEATURE:
        ( A ) NAME/KEY: mat_peptide
        ( B ) LOCATION: 179..499

( x i ) SEQUENCE DESCRIPTION: SEQ ID NO: 4:

| | | | | | | |
|---|---|---|---|---|---|---|
| AAGCGGCGGA | GACAGGATCG | AGAACACAGG | TTTCCTTGAT | ATTCAGCCTG | GAAGGAGGGC | 60 |
| AGGAGGAGCC | CAGAGACCTC | GTTCTTCACT | TGGTCATTCT | CAGTCCATG | ATG GTG | 115 |
| | | | | | Met Val | |
| | | | | | -23 | |

| | | | | | | | | | | | | | | | | |
|---|---|---|---|---|---|---|---|---|---|---|---|---|---|---|---|---|
| TGG | TCC | CCA | GTG | CTC | CTT | GGC | ATC | GTC | GTC | TTG | TCT | GTT | TTT | TCA | GGG | 163 |
| Trp | Ser | Pro | Val | Leu | Leu | Gly | Ile | Val | Val | Leu | Ser | Val | Phe | Ser | Gly | |
| -20 | | | | | -15 | | | | | -10 | | | | | | |
| CCT | AGC | AGG | GCT | GAT | CGA | GCT | ATG | CCC | AAG | CTG | GCT | GAC | TGG | AAG | CTG | 211 |
| Pro | Ser | Arg | Ala | Asp | Arg | Ala | Met | Pro | Lys | Leu | Ala | Asp | Trp | Lys | Leu | |
| -5 | | | | | 1 | | | | 5 | | | | | 10 | | |
| TGT | GCG | GAC | GAG | GAA | TGC | AGC | CAT | CCT | ATC | TCC | ATG | GCT | GTG | GCC | CTC | 259 |
| Cys | Ala | Asp | Glu | Glu | Cys | Ser | His | Pro | Ile | Ser | Met | Ala | Val | Ala | Leu | |
| | | | 15 | | | | | 20 | | | | | 25 | | | |
| CAG | GAC | TAC | GTG | GCC | CCT | GAT | TGC | CGC | TTC | TTG | ACT | ATA | TAT | AGG | GGC | 307 |
| Gln | Asp | Tyr | Val | Ala | Pro | Asp | Cys | Arg | Phe | Leu | Thr | Ile | Tyr | Arg | Gly | |
| | | 30 | | | | | 35 | | | | | 40 | | | | |
| CAA | GTG | GTG | TAT | GTC | TTC | TCC | AAG | TTG | AAG | GGC | CGT | GGG | CGC | CTT | TTC | 355 |
| Gln | Val | Val | Tyr | Val | Phe | Ser | Lys | Leu | Lys | Gly | Arg | Gly | Arg | Leu | Phe | |
| | 45 | | | | | 50 | | | | | 55 | | | | | |
| TGG | GGA | GGC | AGT | GTT | CAG | GGA | GGT | TAC | TAT | GGA | GAC | CTG | GCA | GCC | CGC | 403 |
| Trp | Gly | Gly | Ser | Val | Gln | Gly | Gly | Tyr | Tyr | Gly | Asp | Leu | Ala | Ala | Arg | |
| 60 | | | | | 65 | | | | | 70 | | | | | 75 | |
| CTG | GGC | TAT | TTC | CCC | AGT | AGC | ATT | GTC | CGG | GAG | GAC | CTG | AAC | TCG | AAA | 451 |
| Leu | Gly | Tyr | Phe | Pro | Ser | Ser | Ile | Val | Arg | Glu | Asp | Leu | Asn | Ser | Lys | |
| | | | | 80 | | | | | 85 | | | | | 90 | | |
| CCT | GGC | AAA | ATT | GAT | ATG | AAG | ACC | GAT | CAA | TGG | GAT | TTC | TAC | TGC | CAG | 499 |
| Pro | Gly | Lys | Ile | Asp | Met | Lys | Thr | Asp | Gln | Trp | Asp | Phe | Tyr | Cys | Gln | |
| | | | 95 | | | | | 100 | | | | | 105 | | | |

TGAGCTCAGC CTACCGCTAT CCCTGCAGTT ACCTTCCGGC TCTATGCAAA TACAGCAGCC  559

AATGGCAAAA AAAAAAAAA AA  581

( 2 ) INFORMATION FOR SEQ ID NO: 5:

( i ) SEQUENCE CHARACTERISTICS:
        ( A ) LENGTH: 130 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 5:

| | | | | | | | | | | | | |
|---|---|---|---|---|---|---|---|---|---|---|---|---|
| Met | Val | Trp | Ser | Pro | Val | Leu | Leu | Gly | Ile | Val | Val | Leu | Ser | Val | Phe |
| -23 | | | -20 | | | | | -15 | | | | | -10 | | |
| Ser | Gly | Pro | Ser | Arg | Ala | Asp | Arg | Ala | Met | Pro | Lys | Leu | Ala | Asp | Trp |
| | | -5 | | | | | 1 | | | | 5 | | | | |
| Lys | Leu | Cys | Ala | Asp | Glu | Glu | Cys | Ser | His | Pro | Ile | Ser | Met | Ala | Val |
| 10 | | | | | 15 | | | | | 20 | | | | | 25 |
| Ala | Leu | Gln | Asp | Tyr | Val | Ala | Pro | Asp | Cys | Arg | Phe | Leu | Thr | Ile | Tyr |
| | | | | 30 | | | | | 35 | | | | | 40 | |
| Arg | Gly | Gln | Val | Val | Tyr | Val | Phe | Ser | Lys | Leu | Lys | Gly | Arg | Gly | Arg |
| | | | 45 | | | | | 50 | | | | | 55 | | |
| Leu | Phe | Trp | Gly | Gly | Ser | Val | Gln | Gly | Gly | Tyr | Tyr | Gly | Asp | Leu | Ala |
| | | 60 | | | | | 65 | | | | | 70 | | | |
| Ala | Arg | Leu | Gly | Tyr | Phe | Pro | Ser | Ser | Ile | Val | Arg | Glu | Asp | Leu | Asn |
| | 75 | | | | | 80 | | | | | 85 | | | | |
| Ser | Lys | Pro | Gly | Lys | Ile | Asp | Met | Lys | Thr | Asp | Gln | Trp | Asp | Phe | Tyr |
| 90 | | | | | 95 | | | | | 100 | | | | | 105 |
| Cys | Gln | | | | | | | | | | | | | | |

( 2 ) INFORMATION FOR SEQ ID NO: 6:

( i ) SEQUENCE CHARACTERISTICS:
        ( A ) LENGTH: 31 base pairs
        ( B ) TYPE: nucleic acid ( C ) STRANDEDNESS: single
( D ) TOPOLOGY: linear ( i i ) MOLECULE TYPE: cDNA ( i x ) FEATURE:
    ( A ) NAME/KEY: -
    ( B ) LOCATION: one-of(14, 17, 20)
    ( D ) OTHER INFORMATION: /label=N
       / note= "N denotes I (inosin)"

( x i ) SEQUENCE DESCRIPTION: SEQ ID NO: 6:

```
TGTGAATTCA GTTNWSNGCN GAYCARGART G                                          31
```

( 2 ) INFORMATION FOR SEQ ID NO: 7:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 7:

```
TGTGTCGACT GTTCGTAGAA RTCCATCTT RTC                                         33
```

( 2 ) INFORMATION FOR SEQ ID NO: 8:

( i ) SEQUENCE CHARACTERISTICS:
    ( A ) LENGTH: 305 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_RNA
    ( B ) LOCATION: join(1..29, 277..305)
    ( D ) OTHER INFORMATION: /function="Primer"

( x i ) SEQUENCE DESCRIPTION: SEQ ID NO: 8:

```
GAATTCAAGT TTTCGGCGGA TCAGGAGTGC AGCCACCCTA TCTCCATGGC TGTGGCCCTT            60
CAGGACTACA TGGCCCCCGA CTGCCGATTC CTGACCATTC ACCGGGGCCA AGTGGTGTAT           120
GTCTTCTCCA AGCTGAAGGG CCGTGGGCGG CTCTTCTGGG GAGGCAGCGT TCAGGGAGAT           180
TACTATGGAG ATCTGGTCGC TCGCCTGGGC TATTTCCCCA GTAGCATTGT CCGAGAGGAC           240
CAGACCCTGA AACCTGGCAA AGTCGATGTG AAGACAGATA AATGGGATTT CTACGAACAG           300
TCGAC                                                                     305
```

( 2 ) INFORMATION FOR SEQ ID NO: 9:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 9:

```
GATGCATGCG GTCCTATGCC CAAGCTG                                               27
```

( 2 ) INFORMATION FOR SEQ ID NO: 10:

( i ) SEQUENCE CHARACTERISTICS:
    ( A ) LENGTH: 27 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 10:

GATAAGCTTT CACTGGCAGT AGAAATC    27

(2) INFORMATION FOR SEQ ID NO: 11:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 11:

GATCTAGCCG GCCGCCCAGC CCGGCATG    28

(2) INFORMATION FOR SEQ ID NO: 12:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 12:

CCGGGCTGGG CGGCCGGCTA    20

(2) INFORMATION FOR SEQ ID NO: 13:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 13:

Met Arg Gly Ser His His His His His His Gly Ser Ser Arg Pro Pro
1               5                   10                  15

(2) INFORMATION FOR SEQ ID NO: 14:

(i) SEQUENCE CHARACTERISTICS:
(A) LENGTH: 18 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 14:

Met Arg Gly Ser His His His His His His Gly Ser Val Asp Asp Asp
1               5                   10                  15

Asp Lys (2) INFORMATION FOR SEQ ID NO: 15:

(i) SEQUENCE CHARACTERISTICS:
(A) LENGTH: 43 base pairs
(B) TYPE: nucleic acid (C) STRANDEDNESS: single
(D) TOPOLOGY: linear (ii) MOLECULE TYPE: cDNA (xi) SEQUENCE DESCRIPTION: SEQ ID NO: 15:

AAAAAGGATC CAGCCGGCCG CCCGGTCCTA TGCCCAAGCT GGC  43

(2) INFORMATION FOR SEQ ID NO: 16:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 16:

GGCGAGCAGC CAGATCTCCA TAG  23

(2) INFORMATION FOR SEQ ID NO: 17:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 17:

AAAAAGGAT CCGTTGATGA TGACGATAAA GGTCCTATGC CCAAGCTGGC  50

(2) INFORMATION FOR SEQ ID NO: 18:

(i) SEQUENCE CHARACTERISTICS:
(A) LENGTH: 330 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: mat_peptide
(B) LOCATION: 7..327

(ix) FEATURE:
(A) NAME/KEY: misc_RNA
(B) LOCATION: 4..6
(D) OTHER INFORMATION: /function="Startcodon Met"

(xi) SEQUENCE DESCRIPTION: SEQ ID NO: 18:

CATATGGGAC CAATGCCAAA ATTAGCAGAT CGTAAATTAT GTGCAGATCA GGAGTGCAGC  60
CACCCTATCT CCATGGCTGT GGCCCTTCAG GACTACATGG CCCCGACTG CCGATTCCTG  120
ACCATTCACC GGGGCCAAGT GGTGTATGTC TTCTCCAAGC TGAAGGCCG TGGGCGGCTC  180
TTCTGGGGAG GCAGCGTTCA GGGAGATTAC TATGGAGATC TGGCTGCTCG CCTGGGCTAT  240
TTCCCCAGTA GCATTGTCCG AGAGGACCAG ACCCTGAAAC CTGGCAAAGT CGATGTGAAG  300
ACAGACAAAT GGGATTTCTA CTGCCAGTGA  330

(2) INFORMATION FOR SEQ ID NO: 19:

(i) SEQUENCE CHARACTERISTICS:
(A) LENGTH: 59 base pairs
(B) TYPE: nucleic acid
(C) STRANDEDNESS: single (D) TOPOLOGY: linear (ii) MOLECULE TYPE: cDNA (xi) SEQUENCE DESCRIPTION: SEQ ID NO: 19:

| AAAACATAT | GGGACCAATG | CCAAAATTAG | CAGATCGTAA | ATTATGTGCA | GATCAGGAG | 59 |

(2) INFORMATION FOR SEQ ID NO: 20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

| AAAAAAGCT | TTCACTGGCA | GTAGAAATC | 29 |

(2) INFORMATION FOR SEQ ID NO: 21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

| CGTGAATTCA | ACATGGCCCG | GTCCCTGGTG | TGC | 33 |

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

| TATCTGCAGT | CACTGGCAGT | AGAAATCCCA | 30 |

(2) INFORMATION FOR SEQ ID NO: 23:

(i) SEQUENCE CHARACTERISTICS:
        (A) LENGTH: 260 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

| GTGGGAGGTC | TATATAAGCA | GAGCTCTCTG | GCTAACTAGA | GAACCCACTG | CTTAACTGGC | 60 |
| TTATCGAAAT | TAATACGACT | CACTATAGGG | AGACCCAAGC | TGTACCAGAT | ATCAGGATCC | 120 |
| CCCGGGCTGC | AGGAATTCGA | TATCAAGCTT | CTCGAGGGGG | GGCCCGGTAC | CGATCCTGGC | 180 |
| CAGCTAGCTA | GTAGCTAGAG | GATCTTTGTG | AAGGAACCTT | ACTTCTGTGG | TGTGACATAA | 240 |
| TTGGACAAAC | TACCTACAGA | | | | | 260 |

(2) INFORMATION FOR SEQ ID NO: 24:

(i) SEQUENCE CHARACTERISTICS:

(A) LENGTH: 596 base pairs
(B) TYPE: nucleic acid
(C) STRANDEDNESS: single
(D) TOPOLOGY: linear (ii) MOLECULE TYPE: DNA (genomic)

(ix) FEATURE:
    (A) NAME/KEY: CDS
    (B) LOCATION: join(40..111, 40..166, 214..347, 393..503, 549..569)

(ix) FEATURE:
    (A) NAME/KEY: sig_peptide
    (B) LOCATION: 40..111

(ix) FEATURE:
    (A) NAME/KEY: exon
    (B) LOCATION: 40..166

(ix) FEATURE:
    (A) NAME/KEY: exon
    (B) LOCATION: 214..347

(ix) FEATURE:
    (A) NAME/KEY: exon
    (B) LOCATION: 393..503

(ix) FEATURE:
    (A) NAME/KEY: exon
    (B) LOCATION: 549..569

(ix) FEATURE:
    (A) NAME/KEY: -
    (B) LOCATION: one-of(194, 369, 527)
    (D) OTHER INFORMATION: /note= "N in positions 194, 369 and 527 denotes an indefinite number and sequence of nucleotides"

(xi) SEQUENCE DESCRIPTION: SEQ ID NO: 24:

```
CCAGCACCCC CTTGCTCACT CTCTTGCTCA CAGTCCACGA TGGCCCGGTC CTGGTGTGC      60
CTTGGTGTCA TCATCTTGCT GTCTGCCTTC TCCGGACCTG GTGTCAGGGG TGGTCCTATG    120
CCCAAGCTGG CTGACCGGAA GCTGTGTGCG GACCAGGAGT GCAGCCGTAA GAATGGGGAG    180
GGTAGAATTG GGNCCCTTCT ATTCCTTCCC TAGACCCTAT CTCCATGGCT GTGGCCCTTC    240
AGGACTACAT GGCCCCCGAC TGCCGATTCC TGACCATTCA CCGGGGCCAA GTGGTGTATG    300
TCTTCTCCAA GCTGAAGGGC CGTGGGCGGC TCTTCTGGGG AGGCAGCGTG GGTCTTGGGA    360
GAGTGAAANA GCTTTTAACT CCTCTTCCCC AGGTTCAGGG AGATTACTAT GGAGATCTGG    420
CTGCTCGCCT GGGCTATTTC CCCAGTAGCA TTGTCCGAGA GGACCAGACC CTGAAACCTG    480
GCAAAGTCGA TGTGAAGACA GACGTGGAGT GTCATGGGGG CTGGCANTTT CCCCTTTCTC    540
TTTTTCAGAA ATGGGATTTC TACTGCCAGT GAGCTCAGCC TACCGCTGGC CCTGCC        596
```